United States Patent [19]

Schwaiger et al.

[11] Patent Number: 4,895,954
[45] Date of Patent: Jan. 23, 1990

[54] PRECURSORS FOR SYNTHESIS OF TRIPHENDIOXAZINE DYESTUFFS

[75] Inventors: Günther Schwaiger, Frankfurt am Main; Hartmut Springer, Königstein/Taunus; Walter Helmling, Hofheim am Taunus, all of Fed. Rep. of Germany

[73] Assignee: Hoechst Aktiengesellschaft, Frankfurt am Main, Fed. Rep. of Germany

[21] Appl. No.: 263,733

[22] Filed: Oct. 28, 1988

Related U.S. Application Data

[62] Division of Ser. No. 76,927, Jul. 23, 1987, Pat. No. 4,816,574.

[30] Foreign Application Priority Data

Jul. 26, 1986 [DE] Fed. Rep. of Germany ....... 3625346

[51] Int. Cl.$^4$ ............................................ C07D 249/18
[52] U.S. Cl. .................................... 548/260; 544/337; 544/366; 548/113; 548/261
[58] Field of Search ................ 544/337, 366; 548/113, 548/260, 261

[56] References Cited

PUBLICATIONS

Katritzky et al., Chemical Abstracts, vol 107 (1987) 198190f.

Primary Examiner—Richard L. Raymond

[57] ABSTRACT

Water-soluble triphendioxazine compounds which have fiber-reactive properties as dyestuffs, which afford deep and fast dyeings on fiber materials, such as wool and, in particular, cellulose, and which correspond to the formula (1)

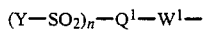

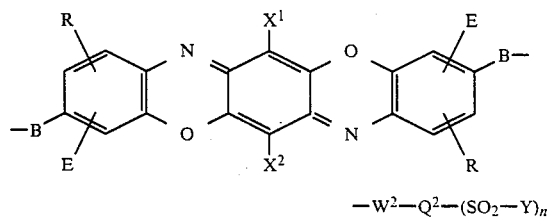

in which:

n is the number 0 or 1;

Y is the vinyl group or an ethyl group containing, in β-position, a substituent which can be eliminated by means of an alkali;

$Q^1$ and $Q^2$ both represent a benzotriazole radical which can also be additionally substituted in the benzene nucleus by alkyl having 1 to 4 carbon atoms, alkoxy having 1 to 4 carbon atoms, halogen, carboxy or sulfo;

B is —O—, —S—, —NH— or —N(R')— wherein R' is optionally substituted alkyl having 1 to 6 carbon atoms;

$W^1$ and $W^2$ both represent a divalent, optionally substituted aliphatic, cycloaliphatic, aliphatic-cycloaliphatic, araliphatic or aromatic-carbocyclic radical, it being possible for the aliphatic radicals to be interrupted by hetero groups —O—, —S—, —SO$_2$—, —CO—, 1,4-piperidino, —NH— and/or —N(R$^o$)— in which R$^o$ is optionally substituted alkyl having 1 to 6 carbon atoms or alkanoyl having 2 to 5 carbon atoms, and/or for aliphatic and aryl radicals to be attached to one another through such a hetero group;

R is hydrogen, alkyl having 1 to 6 carbon atoms, alkoxy having 1 to 6 carbon atoms, halogen, carboxyl or sulfo;

E is hydrogen, sulfo, carboxyl, a group —SO$_2$—Y as defined above or an optionally substituted sulfonamide group; and $X^1$ and $X^2$ are both hydrogen or halogen, cycloalkyl, alkoxy, aryloxy, aryl or another substituent;

and at least one carboxy, sulfo or sulfato group is present in the molecule (1), and pre-products of those triphendioxazine compounds, of the general formula

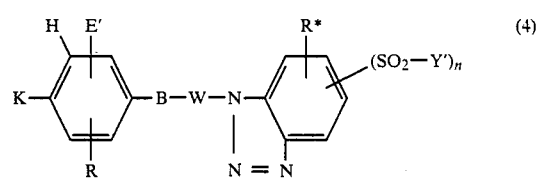

in which K is an amino or nitro group, Y' is β-hydroxyethyl or defined as for Y, W has one of the meanings of $W^1$, and E' is hydrogen, sulfo, carboxy or a group of the formula —SO$_2$—Y' defined above, or an optionally substituted sulfonamide group, and R, B and R* have the above meanings.

19 Claims, No Drawings

PRECURSORS FOR SYNTHESIS OF TRIPHENDIOXAZINE DYESTUFFS

This is a division of our copending application Ser. No. 076,927, filed July 23, 1987, now U.S. Pat. No. 4,816,574.

The present invention is within the field of fiber-reactive dyestuffs.

Fiber-reactive triphendioxazine dyestuffs in which the fiber-reactive groups are, however, not attached to a heterocyclic radical are already known from European Patent Application Publications Nos. 0,141,966 A and 0,168,751 A and U.S. Pat. No. 4,577,015.

New water-soluble triphendioxazine compounds corresponding to the general formula (1)

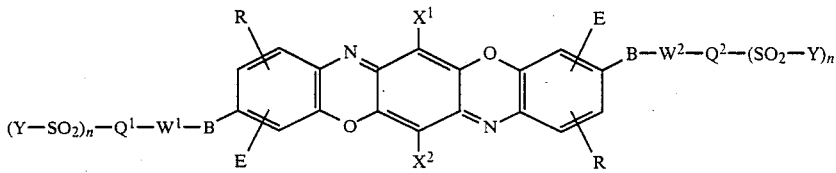

which possess valuable fiber-reactive dyestuff properties have now been found.

The symbols in this formula (1) have the following meanings:

n is the number 0 or 1, preferably 1, the group $-SO_2-Y$ representing a hydrogen atom if n=0, and n is only zero if E is a group $-SO_2-Y$ in which Y is β-sulfatoethyl;

Y is the vinyl group or an ethyl group containing, in the β-position, a substituent which can be elminated by means of an alkali;

$Q^1$ is a benzotriazole radical of the general formula (2a) indicated below and $Q^2$ is a benzotriazole radical of the general formula (2b) indicated below

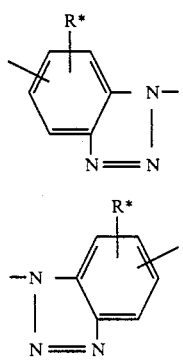

in which

R* denotes a hydrogen atom, an alkyl group having 1 to 4 carbon atoms, such as the methyl or ethyl group, an alkoxy group having 1 to 4 carbon atoms, such as the methoxy or ethoxy group, a halogen atom, such as a chlorine atom, or a carboxy or sulfo group, but preferably denotes a hydrogen atom, and the free bond on the benzene radical characterizes the bond leading to the grouping $(Y-SO_2)_n$, B is an oxygen or sulfur atom or an amino group of the formula $-NH-$, preferably the amino group $-NH-$, or is a group of the formula $-N(R')-$ in which R′ is an alkyl group which has 1 to 6 carbon atoms, preferably 1 to 4 carbon atoms, such as, in particular, the methyl or ethyl group, and which can be substituted;

$W^1$ is a divalent, optionally substituted aliphatic radical, ($C_5-C_{10}$)-cycloaliphatic radical which is optionally substituted by alkyl, aliphatic-($C_5-C_8$)-cycloaliphatic radical which is optionally substituted by alkyl, optionally substituted araliphatic radical or optionally substituted aromatic-carbocyclic radical, it being possible for the aliphatic radicals in $W^1$ to be interrupted by hetero groups, preferably 1 to 2 hetero groups, selected from the groups $-O-$, $-S-$, $-SO_2-$, $-CO-$, 1,4-piperidino, $-NH-$ and $-N(R^o)-$, wherein $R^o$ is an alkyl group having 1 to 6 carbon atoms, preferably 1 to 4 carbon atoms, such as, in particular, the methyl or ethyl group, and which can be substituted, or is an alkanoyl group having 2 to 5 carbon atoms, such as the acetyl group, and/or the aliphatic and aryl moieties may be attached to one another by such a hetero group;

$W^2$ has a meaning indicated for $W^1$ and is identical with $W^1$ or different from $W^1$;

R is a hydrogen atom or an alkyl group having 1 to 6 carbon atoms, preferably 1 to 4 carbon atoms, such as methyl and ethyl, an alkoxy group having 1 to 5 carbon atoms, preferably 1 to 4 carbon atoms, such as methoxy and ethoxy, a halogen atom, such as fluorine and bromine and especially chlorine, carboxy or sulfo, preferably a hydrogen atom;

E is a hydrogen atom or a sulfo or carboxy group or a group of the general formula $-SO_2-Y$ in which Y has the meaning indicated later or is an optionally substituted sulfoamide group, but is particularly a sulfo group;

$X^1$ is a hydrogen atom or a halogen atom, such as fluorine and, in particular, a chlorine or bromine atom, a cycloalkyl group having 5 to 8 carbon atoms, such as the cyclohexyl group, an aralkyloxy group, an alkoxy group having 1 to 4 carbon atoms, such as the methoxy group, an aryloxy group, an alkyl group having 1 to 4 carbon atoms, such as the methyl group, an aryl group, an aralkyl group, a cyano group, a carboxy group, a carboalkoxy group having 2 to 5 carbon atoms, such as the carbomethoxy or carboethoxy group, an arylamino group, a carbamoyl group, an N-alkylcarbamoyl group or N,N-dialkylcarbamoyl group in which the alkyl radicals each have 1 to 4 carbon atoms, an N-arylcarbamoyl group, an alkanoylamino group having 2 to 5 carbon atoms, such as the acetylamino group, or an aroylamino group, such as the benzoylamino group, the aryl radicals in these named substituents being preferably phenyl radicals which can also be substituted by 1 or 2 substituents belonging to the group comprising halogen, such as chlorine, nitro, alkyl having 1 to 4 carbon atoms, alkoxy having 1 to 4 carbon atoms, carboxy and sulfo, and $X^1$ being preferably a hydrogen atom, an alkanoylamino group having 2 to 5 carbon atoms, a phenoxy group which can be substituted, an alkoxy group having 1 to 4 carbon atoms, an alkyl group having 1 to 4 carbon atoms and, particularly preferably, a chlorine atom or bromine atom;

$X^2$ is identical with $X^1$ or different from $X^1$ and has one of the meanings indicated for $X^1$;

the group E is preferably attached in the ortho-position relative to the group $-B-W^1-Q^1-(SO_2-Y)_n$ or $-B-W^2-Q^2-(SO_2-Y)_n$; and the molecule (1) must contain at least one, preferably at least two, of the carboxy, sulfo and sulfato groups which can be present in the molecule (1).

The individual structural members, including those occurring twice, can have meanings which are identical with one another or different from one another.

Aryl radicals in the groups mentioned above or below are, in particular, the phenyl and naphthyl radicals; they can be substituted, for example by substituents belonging to the group comprising alkyl having 1 to 4 carbon atoms, such as methyl and ethyl, alkoxy having 1 to 4 carbon atoms, such as methoxy and ethoxy, halogen, such as chlorine and bromine, sulfo, carboxy, sulfamoyl, carbamoyl, carbamoyl which monosubstituted or disubstituted by phenyl, alkyl having 1 to 4 carbon atoms, phenylalkyl containing an alkyl radical having 1 to 4 carbon atoms and/or cycloalkyl having 5 to 8 carbon atoms, sulfamoyl which is monosubstituted or disubstituted by phenyl, alkyl having 1 to 4 carbon atoms, phenylalkyl containing an alkyl radical having 1 to 4 carbon atoms and/or cycloalkyl having 5 to 8 carbon atoms, trifluoromethyl, benzoylamino, sulfobenzoylamino, alkanolyamino having 2 to 5 carbon atoms, nitro, amino and amino which is optionally monosubstituted or disubstituted, the substituents thereof being optionally substituted aliphatic (including araliphatic) radicals or optionally substituted aryl and $(C_5$-$C_8)$-cycloalkyl radicals.

Aryl radicals in the araliphatic radicals are, in particular, phenylene and naphthylene radicals; they can be substituted, for example by substituents belonging to the group comprising alkyl having 1 to 4 carbon atoms, such as methyl and ethyl, alkoxy having 1 to 4 carbon atoms, such as methoxy and ethoxy, halogen, such as chlorine and bromine, sulfo, carboxy, sulfamoyl, carbamoyl, carbamoyl which is monosubstituted or disubstituted by phenyl, alkyl having 1 to 4 carbon atoms, phenylalkyl containing an alkyl radical having 1 to 4 carbon atoms and/or cycloalkyl having 5 to 8 carbon atoms, sulfamoyl which is monosubstituted or disubstituted by phenyl, alkyl having 1 to 4 carbon atoms, phenylalkyl containing an alkyl radical having 1 to 4 carbon atoms and/or cycloalkyl having 5 to 8 carbon atoms, trifluoromethyl, benzoylamino, sulfobenzoylamino, alkanoylamino having 2 to 5 carbon atoms, nitro, amino and amino which is optionally monosubstituted or disubstituted, the substituents thereof being optionally substituted aliphatic (including araliphatic) radicals or optionally substituted aryl and $(C_5$-$C_8)$-cycloalkyl radicals.

Examples of aromatic-carbocyclic radicals are phenylene and naphthylene or phenyl and naphthyl radicals which can be substituted, for example by substituents from the group comprising alkyl having 1 to 4 carbon atoms, such as methyl and ethyl, alkoxy having 1 to 4 carbon atoms, such as methoxy and ethoxy, halogen, such as chlorine and bromine, sulfo, carboxy, sulfamoyl, carbamoyl, carbamoyl which is monosubstituted or disubstituted by phenyl, alkyl having 1 to 4 carbon atoms, phenylalkyl containing an alkyl radical having 1 to 4 carbon atoms and/or cycloalkyl having 5 to 8 carbon atoms, sulfamoyl which is monosubstituted or disubstituted by phenyl, alkyl having 1 to 4 carbon atoms, phenylalkyl containing an alkyl radical having 1 to 4 carbon atoms and/or cycloalkyl having 5 to 8 carbon atoms, trifluoromethyl, benzoylamino, sulfobenzoylamino, alkanoylamino having 2 to 5 carbon atoms, nitro, amino and amino which is optionally monosubstituted or disubstituted, the substituents thereof being optionally substituted aliphatic (including araliphatic) radicals or optionally substituted aryl and $(C_5$-$C_8)$-cycloalkyl radicals. Preferred representatives of these are, in particular, phenylene or phenyl radicals which can be substituted by substituents belonging to the group comprising alkyl having 1 to 4 carbon atoms, alkoxy having 1 to 4 carbon atoms and sulfo and/or by an amino group which is optionally monosubstituted or disubstituted, for ex. by alkyl of 1 to 4 C-atoms, phenyl and/or benzyl.

Examples of aliphatic radicals are alkyl groups or alkylene groups which have in each case 1 to 6 carbon atoms, preferably 1 to 4 carbon atoms, and can be substituted. Examples of substituted alkyl and alkylene groups are groups which can be substituted by 1 or 2 substituents belonging to the group comprising chlorine, alkoxy having 1 to 4 carbon atoms, benzoylamino, sulfobenzoylamino, alkanoylamino having 2 to 5 carbon atoms, hydroxy, sulfato, phosphato, phosphono, acetyloxy, sulfo, carboxy or optionally substituted aryl. Of these, preferred substituents are the carboxy and sulfo groups and also sulfato groups.

Examples of the structural members $W^1$ and $W^2$ are alkylene groups having 1 to 6 carbon atoms, in particular 2 to 4 carbon atoms, in which the alkylene chain can be interrupted by 1 or 2 hetero groups, preferably selected from the groups $-O-$, $-NH-$ and $-N(R')-$ in which $R'$ has the above meaning, or are, for ex., an alkylenephenylene, phenylenealkylene, phenylenealkylenephenylene or alkylenephenylenealkylene radical, the alkylene moieties of which have 1 to 6, preferably 1 to 4 carbon atoms, and can optionally be substituted by the substituents indicated and/or interrupted by 1 or 2 of the hetero groups mentioned, and each of the benzene nuclei can also be substituted by 1 or 2 substituents selected from the group of substituents comprising sulfo, carboxy, sulfamoyl, carbamoyl, methyl, ethyl, methoxy, ethoxy, nitro, chlorine, amino and amino which is substituted by optionally substituted aliphatic radicals and/or optionally substituted aryl radicals, and, in the event that an alkylene group is interrupted by hetero groups, its alkylene constituents preferably have 2 or 3 carbon atoms, and the aliphatic and aryl radical can also be attached through an oxygen atom or a group $-NH-$. Further examples of the structural members $W^1$ and $W^2$ are a phenylene radical, in particular a meta-phenylene or paraphenylene radical, which can also be substituted by 1 or 2 substituents belonging to the group comprising sulfo, carboxy, sulfamoyl, carbamoyl, methyl, ethyl, methoxy, ethoxy, chorine, amino and amino which is substituted by optionally substituted aliphatic radicals and/or optionally substituted aryl radicals, sulfo being preferred, or a naphthylene radical which is optionally substituted by sulfo. $W^1$ and/or $W^2$ are preferably an alkylene radical which has 2 or 4 carbon atoms and which can be substituted by 1 or 2 substituents, preferably one substituent, belonging to the group comprising sulfo, sulfato, carboxyl, phenyl and sulfophenyl, it being also possible for the alkylene radicals to be attached through an oxygen atom or a group —NH—, or are preferably an alkylenephenylene radical containing such alkylene radicals.

The fiber-reactive groups of the formula —SO$_2$—Y are attached to the aromatic carbon atoms of the benzene radicals of the benzotriazole, respectively phenoxyazine; the group —SO$_2$—Y is preferably in the 5-position in the benzo-1,2,3-triazole radicals Q$^1$ or Q$^2$.

Examples of radicals W$^2$ are the meta-phenylene or paraphenylene radical and the 1,2-ethylene, 1,3-propylene, 1,4-butylene, 1,5-pentylene, 1,6-hexylene, 2-methyl-1,3-propylene, 2-sulfophenyl-1,3-propylene and 2-sulfato-1,3-propylene radical; further examples are a sulfosubstituted 1,4-phenylene radical, a 1,4-cyclohexylene and 1,3-cyclohexylene radical, a divalent radical of the formulae (a) to (z) indicated below, of which preferred the 1,2-ethylene, 1,3-propylene and 1,4-butylene radical, a radical of the formulae (a), a 2-sulfophenyl-1,3-propylene radical, a 2sulfato-1,3-propylene radical and a sulfo-substituted 1,4-phenylene radical:

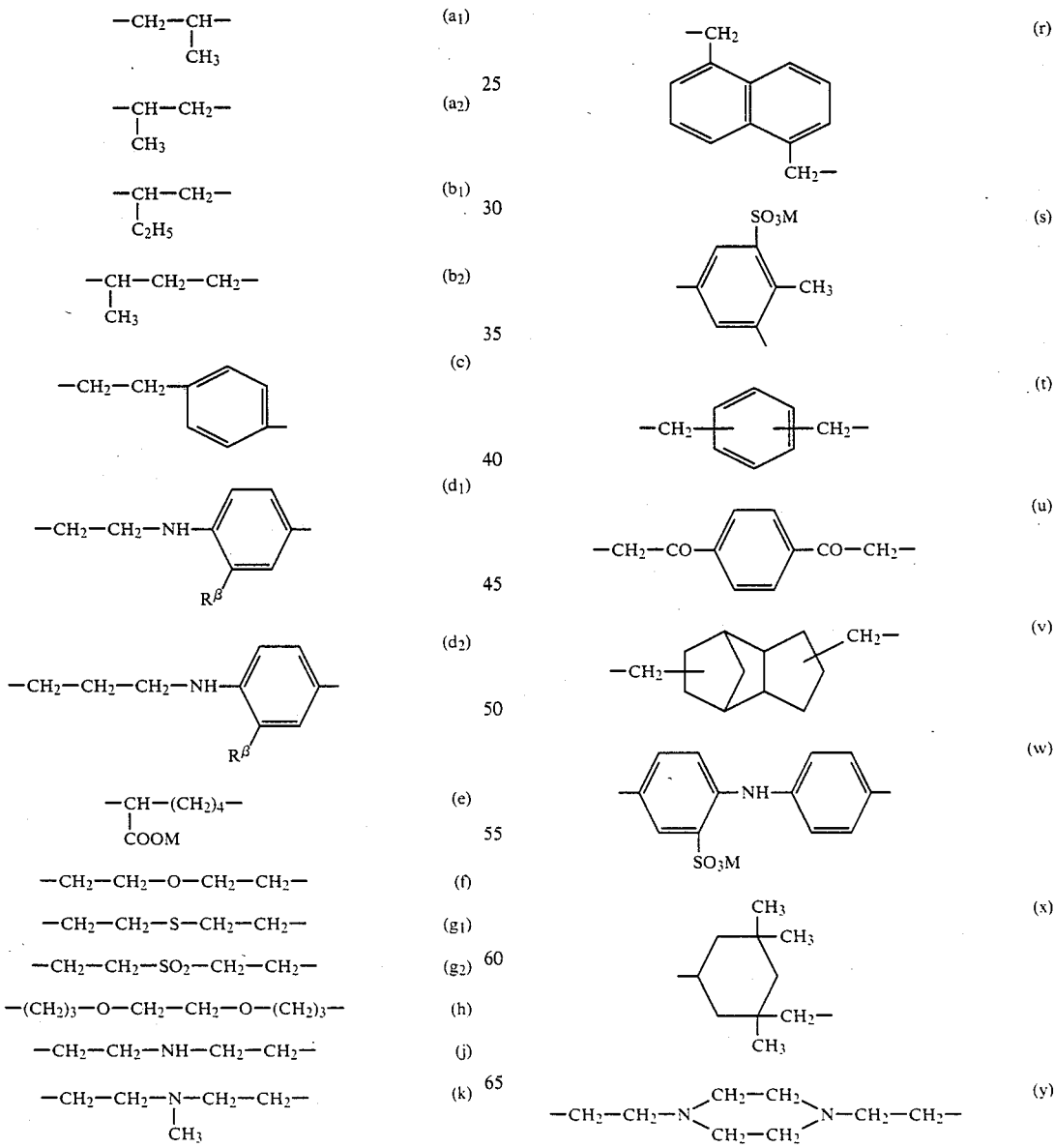

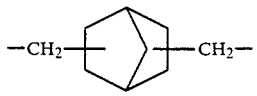 (z)

in which $R^\beta$ is a hydrogen atom or a sulfo group and M is a hydrogen atom or an alkali metal, such as sodium, potassium and lithium, or the equivalent of an alkaline earth metal, such as, for example, calcium, but is especially an alkali metal.

Examples of radicals $W^1$ are those just mentioned for $W^2$, but groups arranged in the manner of an "mirror image".

If the radical E in the formula is a substituted sulfonamide group, its nitrogen atom is monosubstituted or disubstituted by optionally substituted alkyl groups having 1 to 6 carbon atoms (including optionally substituted aralkyl) and by optionally substituted aryl radicals, the substituents preferably being groups imparting solubility in water, such as the sulfo, carboxy, sulfato, phosphato or phosphono group. The optionally substituted sulfonamide group is preferably a group of the general formula $-SO_2-NR^1R^2$ in which $R^1$ is a hydrogen atom or an alkylene group which has 2 to 6 carbon atoms, preferably 2 to 4 carbon atoms, and is substituted by a sulfo or sulfato group, it being also possible for the alkylene group to be interrupted by 1 to 2 hetero groups selected from the groups of the formulae $-O-$, $-S-$, $-NH-$ and $-N(R')-$ in which R' has the meaning indicated above, or $R^1$ is an alkylene radical which has 2 to 6 carbon atoms, preferably 2 to 4 carbon atoms, and is substituted by a carboxy or phosphato group, or $R^1$ is an alkylene radical which has 1 to 3 carbon atoms and is substituted by a phosphono group, or $R^1$ is a naphthyl or phenyl radical both of which can be substituted by substituents belonging to the group comprising methyl, methoxy, ethoxy, chlorine, carboxy and sulfo, the substituents preferably being 1 to 3 sulfo groups, and of these the monosulfophenyl and disulfophenyl radicals being preferred, and in which $R^2$ represents a hydrogen atom or denotes an alkyl group which has 1 to 6 carbon atoms, preferably 2 to 4 carbon atoms, and can be substituted, preferably by 1 or 2, preferably 1, substituents belonging to the group comprising hydroxy, sulfato, carboxy, sulfo and methoxy. Examples of substituted sulfonamide groups are also groups of a general formula $-SO_2-NH-SO_2R^3$ in which $R^3$ denotes an optionally substituted alkyl group having 1 to 6 carbon atoms, preferably 1 to 4 carbon atoms, in particular a methyl group, or represents an optionally substituted aryl radical, the aryl radical being particularly preferably a phenyl radical which can be substituted by 1 or 2 sulfo groups.

The group E is preferably a sulfo group, a carboxy group, an N,N-di-(β-sulfatoethyl)-sulfamoyl group, an N-(β-sulfatoethyl)-sulfamoyl group, an N-(β-sulfoethyl)-sulfamoyl group or a β-sulfatoethylsulfonyl group, the β-sulfatoethylsulfonyl group being obligatory if the index n in formula (1) represents 0; E is particularly preferably a sulfo group.

Substituents which, as defined in the structural member Y, are attached in the β-position of the ethyl group and can be eliminated by an alkali with the formation of the vinyl group, are, for example, alkanoyloxy groups having 2 to 5 carbon atoms, such as the acetoxy group, aroyloxy groups, such as the benzoyloxy, sulfobenzoyloxy or carboxybenzoyloxy group, dialkylamino groups containing alkyl radicals having 1 to 4 carbon atoms, such as, in particular, the dimethylamino and diethylamino group, trialkylammonium groups containing alkyl radicals having 1 to 4 carbon atoms, such as the trimethylammonium group, the chlorine atom, the bromine atom, alkylsulfonyloxy groups containing alkyl radicals having 1 to 4 carbon atoms, a phosphato group, a thiosulfato group or a sulfato group. Of the groups which conform to the structural element Y the β-chloroethyl, β-phosphatoethyl, β-acetoxyethyl and β-thiosulfatoethyl group and, in particular, the vinyl group are preferred, and the β-sulfatoethyl group is very particularly preferred.

The two radicals Y in the general formula (1) can have meanings identical with one another or different from one another; preferably they have the same meaning. Similarly, the radicals $(Y-SO_2)_n-Q^1-W^1-B-$ and $-B-W^2-Q^2-(SO_2-Y)_n$ can have meanings identical with one another or different from one another; preferably they have the same meaning. Similarly, the groups E can have meanings identical with one another or different from one another; preferably they have the same meaning.

Sulfo groups are groups corresponding to the general formula $-SO_3M$, carboxy groups are groups corresponding to the general formula $-COOM$, sulfato groups are groups corresponding to the general formula $-OSO_3M$, phosphono groups are groups of the general formula $-PO_3M_2$, thiosulfato groups are groups corresponding to the general formula $-S-SO_3M$ and phosphato groups are groups corresponding to the general formula $-OPO_3M_2$, M having the meaning mentioned above.

Triphendioxazine compounds according to the invention which should be singled out particularly are those which correspond to the general formula (1a)

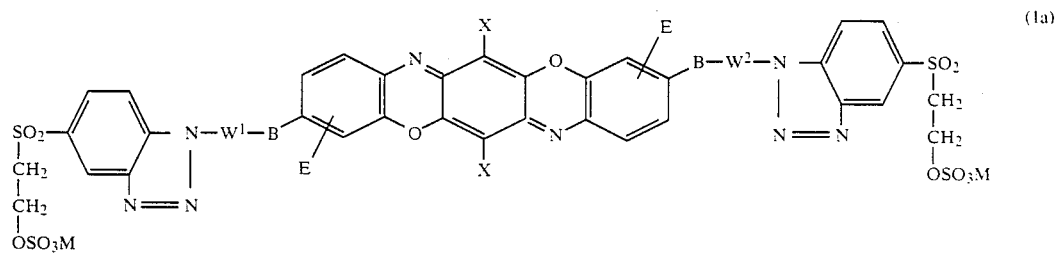 (1a)

in which

X represents a bromine atom or preferably a chlorine atom,

M is a hydrogen atom or preferably an alkali metal atom, such as, in particular, sodium, B represents the group, $-NH-$, $W^2$ is a 1,2-ethylene, 1,3-propylene, 1,4-butylene, 1,6-hexylene, 1,4-cyclohexylene or 1,4-phenylene group or a sulfo-substituted 1,4-phenylene radical or a radical of the formulae (a), (c), (d₁) or (d₂) indicated above, or a radical of the formula (z₁) or (Z₂) below

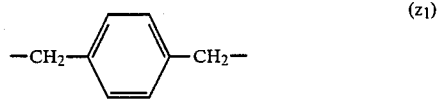

(z₁)

(z₂)

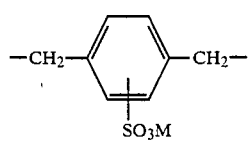

in which M has the meaning mentioned above, the 1,2-ethylene, 1,3-propylene and 1,4-butylene group and the group of the formulae (a) being preferred amongst these, and $W^1$ denotes a radical of the type mentioned for $W^2$, but arranged in the manner of a "mirror image".

In formula (1a) the two radicals E and also the radicals $W^1$ and $W^2$ are, respectively, preferably identical with one another.

Further triphendioxazine compounds according to the invention which can be singled out are those corresponding to a general formula (1b)

B represents the group —NH—, $W^2$ is the 1,2-ethylene or 1,3-propylene or 1,4-cyclohexylene radical or a radical of the formulae (a), (c), (d₁), (d₂) or (Z₂) indicated above, the 1,2-ethylene or 1,3-propylene radical or a radical of the formulae (a) being preferred amongst these, and $W^1$ denotes a radical of the type just mentioned for $W^2$, but arranged in the manner of a "mirror image" thereto, and R* is in each case a sulfo group which is preferably in the 5-position of the benzo-1,2,3-triazole.

Compounds of interest are also those of the general formula (1c)

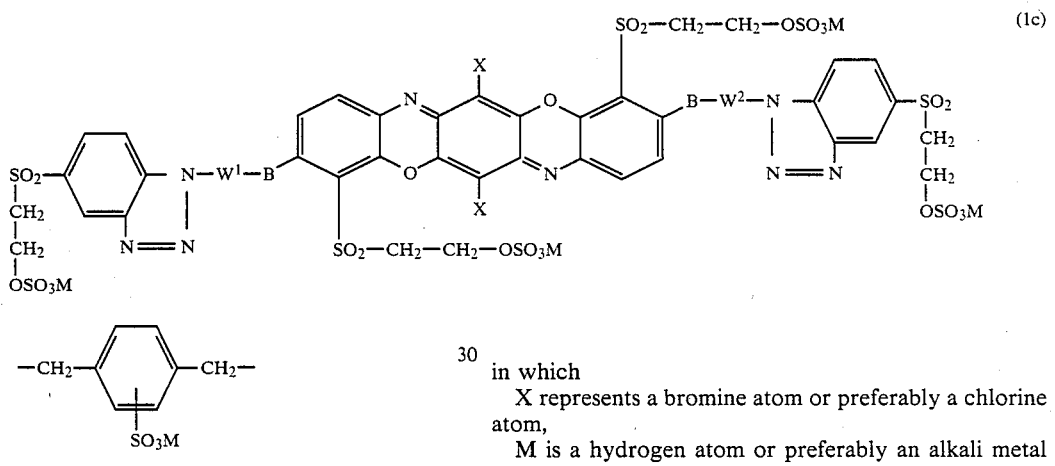

in which

X represents a bromine atom or preferably a chlorine atom,

M is a hydrogen atom or preferably an alkali metal atom, such as, in particular, sodium, B represents the group —NH— and $W^1$ and $W^2$ both denote one of the radicals indicated above containing sulfo groups or sulfato groups.

In the formulae (1b) and (1c), the two R*s and the two groups $W^1$ and $W^2$ preferably have, respectively, an identical meaning.

The new dioxazine compounds can be either in the acid form or in the form of their salts. They are preferably in the form of their salts, in particular the alkali and alkaline earth metal salts, and are also preferably used in the form of these salts for dyeing (to be understood here and in the following text in the general sense and includ-

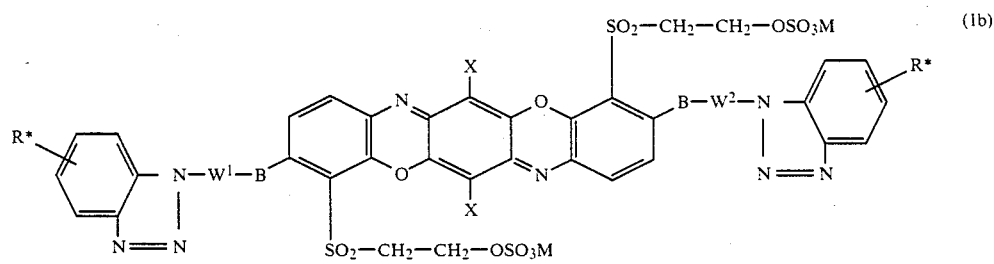

in which

X represents a bromine atom or preferably a chlorine atom,

M is a hydrogen atom or preferably an alkali metal atom, such as, in particular, sodium, ing printing) materials containing hydroxy and/or carboxamide groups, in particular fiber materials.

The present invention also relates to processes for the preparation of the compounds of the general formula (1) mentioned and defined above. These processes comprise cyclizing a compound of the general formula (3)

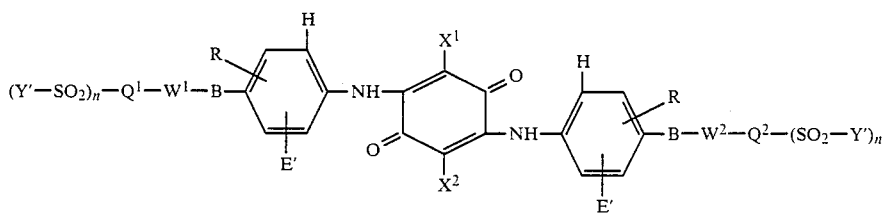

(in which Y' is the vinyl group, the β-hydroxyethyl group or an ethyl group containing, in the β-position, a substituent which can be eliminated by means of an alkali, such as one of the substituents mentioned for Y, and is preferably the β-hydroxyethyl group, and n, R, B, $Q^1$, $Q^2$, $W^1$, $W^2$ $X^1$ and $X^2$ have the meanings mentioned above and E' has one of the meanings mentioned for E or is a β-hydroxyethylsulfonyl group, and substituted alkyl groups in these radicals can also be hydroxy-substituted alkyl groups, the groups E' are preferably attached in the ortho-position relative to the group $(Y'—SO_2)_n—Q^1—W^1—B—$ or $—B—W^2—Q^2—(SO_2—Y')_n$ and the benzene nuclei must not be substituted in one of the ortho-positions relative to the amino group —NH— indicated) in an acid medium and preferably in the presence of an oxidizing agent to give the triphendioxazine. The reaction is carried out by a procedure known per se, for example in sulfuric acid or sulfuric acid containing sulfur trioxide as the reaction medium, the oxidizing agent used being sulfur trioxide, ammonium or alkali metal persulfates, iodine or inorganic iodine compounds in the presence of oleum, and sodium perborate, but preferably sodium or potassium peroxodisulfate (corresponding to the formulae $Na_2S_2O_8$ or $K_2S_2O_8$, respectively). Procedures of this type are disclosed, for example, in British Patent No. 1,589,915 and European Patent Application Publication No. 0,141,359A.

The reaction is preferably carried out in concentrated sulfuric acid, such as 96% strength to, preferably, 100% strength sulfuric acid and, in particular, in sulfuric acid containing sulfur trioxide (oleum), such as oleum up to a strength of 50% by weight. The reaction temperature selected is between 0° and 80° C. The oleum used as the reaction medium and agent as a rule has a sulfur trioxide content of 5 to 40% by weight, preferably 10 to 20% by weight. If peroxodisulfate is added as the oxidizing agent, the cyclization is carried out between 0° and 40° C., preferably between 15° and 25° C. If oleum/peroxodisulfate is used, the reaction temperature should not exceed 30° C. 10 to 20% strength oleum, using an amount of peroxodisulfate equivalent to the compound (3), is preferred.

If iodine is the oxidizing agent, it is employed in catalytic amounts in 10 to 50% strength oleum; in this case the reaction temperature is, as a rule, between 0° and 40° C.

If appropriate, it is possible, before or at the same time as the cyclization or not until after the cyclization reaction, to esterify hydroxyalkyl groups which may be present, such as, for example, the β-hydroxyethyl group of the radical Y', by means of a sulfating or phosphating agent, such as 96–100% strength sulfuric acid or sulfuric acid containing sulfur trioxide or polyphosphoric acid, to give the corresponding β-sulfatoalkyl or β-phosphatoalkyl groups, respectively. If, therefore, the cyclization is carried out in sulfuric acid or oleum as the reaction medium, hydroxy groups attached to an alkyl radical of the molecule, such as, for example, the β-hydroxyethyl groups already mentioned above of the radical Y' or hydroxyalkyl groups of the radicals $W^1$ or $W^2$ and E', are converted into the corresponding sulfatoalkyl groups.

At temperatures above about 35° C., such as temperatures between 40° and 60° C., it is also possible, in accordance with the invention, to introduce sulfo groups into the aromatic rings of the triphendioxazine (including the corresponding aryl radicals of $W^1$, $W^2$, E', $X^1$ and $X^2$).

Compounds of the formula (1) in which Y is a β-sulfatoethyl group can subsequently be converted by known processes into other compounds, according to the invention, of formula (1) in which Y represents the vinyl group or an ethyl group containing another substituent, located in the β-position, which can be eliminated by means of alkali.

The compounds of the general formula (3) can be prepared analagously to known procedures by reacting a compound of the general formula (4)

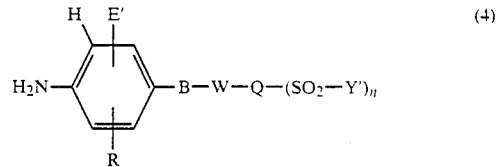

(in which Q has the meaning $Q^1$ or $Q^2$ and W has the meaning $W^1$ or $W^2$ and Y' has the abovementioned meaning and is preferably the β-hydroxyethyl group and n, R, B and E' have the abovementioned meanings, it being also possible for substituted alkyl groups in these radicals to be hydroxy-substituted alkyl groups, and the groups E' being preferably attached in the ortho-position relative to the group B) with a 1,4-benzoquinone compound of the general formula (5)

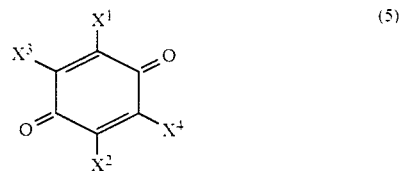

in which $X^1$ and $X^2$ have the meanings mentioned above and $X^3$ and $X^4$ are identical with one another or different from one another and each represents a hydrogen atom, an alkoxy group having 1 to 4 carbon atoms, such as, in particular, the methoxy group, or a phenoxy group or is preferably a halogen atom, such as a fluorine atom, especially a bromine atom and particularly a chlorine atom, it being also possible for $X^3$ and $X^4$ to have the same meaning as $X^1$ and $X^2$.

The reaction of a compound of the general formula (4) or of two different amino compounds of the general formula (4), in each case in an amount which together is twice equivalence, with one equivalent of a compound of the general formula (5) to give the compound of the general formula (3) is carried out analgously to known procedures, which are described, for example, in K. Venkataraman, "The Chemistry of Synthetic Dyes", volume V, pages 419-427 (1971), and in Ullmanns Encyklopädie der technischen Chemie, ("Ullmann's Encyclopedia of Industrial Chemistry"), 4th edition, volume 8, pages 240 and 241 (1974) and in British Patent Application publication No. 2,019,872, in German Offenlegungsschrift No. 2,823,828 and in European Patent Application Publication No. 0,141,996A. For example, the reaction can be carried out in an aqueous medium or in an aqueous-organic medium or in a purely organic medium, the organic solvents being polar, aprotic and protic solvents, such as, for example, lower alkanols, such as methanol and ethanol, and halogenated benzenes, such as o-dichlorobenzene. It is preferable to employ the quinone of the formula (5), but in an excess of varying extent which, as a rule, is 2-20%, but can also be up to 100% or more, depending on the quinone selected. The reaction of the amines (4) with the quinones (5) can be carried out at a temperature between 20° and 100° C., preferably between 50° and 70° C., in the presence of an acid-binding agent, such as, for example, an alkali metal carbonate or acetate or an alkaline earth metal carbonate or acetate, for example sodium acetate, sodium carbonate or sodium bicarbonate, or an alkali or alkaline earth metal hydroxide, such as sodium hydroxide, or an oxide of an alkaline earth metal, such as, for example, magnesium oxide. If the reaction is carried out in an aqueous or aqueous-organic medium, the pH is adjusted to a range between 4 and 7, preferably between 5.5 and 6.5.

The aniline starting compounds of the general formula (4) have not hitherto been known. The invention therefore also relates to these compounds, to processes for their preparation and to their use for the synthesis of dyestuffs. They can be prepared analogously to known procedures for reacting nitrochlorobenzenes with amines, for example by reacting a chloronitrobenzene of the general formula (6)

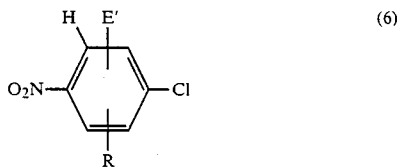
(6)

in which R and E' have the meanings mentioned above, with an amine of the general formula (7)

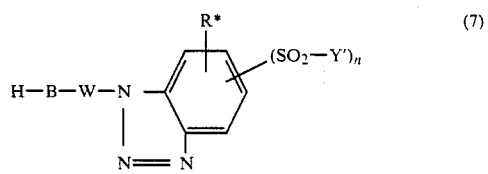
(7)

in which B, R*, W, Y' and n have the meanings mentioned above, in water or an organic medium, such as an alkanol, for example methanol, dioxane and toluene, or in a mixture of water and water-miscible organic solvents, with the addition of a basic, acid-binding agent, such as, for example, potassium carbonate, magnesium oxide, sodium carbonate, sodium hydroxide, triethylamine or triethanolamine, at a temperature between 20° and 140° C., preferably between 70° and 120° C., and under normal pressure or a pressure of up to 50 bar, preferably up to 10 bar. In an aqueous medium, the pH is maintained at a value between 6 and 12, preferably between 8 and 10.

Procedures of this type are known, for example, from the processes for the preparation of substituted phenyl β-hydroxyethyl sulfones (see, for example, German Offenlegungsschrift No. 3,502,991).

The nitroaniline compounds, according to the invention, which can be obtained in this manner and are also new, of the general formula (8)

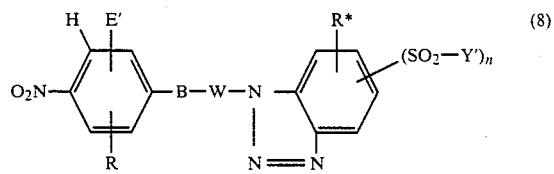
(8)

in which R, R*, E', B, W, Y' and n have the meanings mentioned above, can then be reduced in accordance with methods customary per se for the reduction of aromatic nitro groups, by means of hydrogen and a metallic catalyst, such as a palladium, platinum or Raney nickel catalyst, under pressure in an autoclave, or by means of the Béchamp method of reduction using iron turnings, to give the compound corresponding to the general formula (4) in which Y' preferably represents the β-hydroxyethyl group. From the β-hydroxyethylsulfonyl compounds of the general formula (4) it is possible to prepare the corresponding fiber-reactive starting compounds (4) in which Y' represents the vinyl group or an ethyl group containing, in the β-position, a substituent which can be eliminated by means of alkali, using a generally known procedure for converting the β-hydroxyethylsulfonyl group into groups of this type. It is preferable to convert the β-hydroxyethylsulfonyl group into the β-sulfatoethylsulfonyl group.

The following are examples of chloronitrobenzene compounds of the general formula (6) which can be used as starting compounds: 2-sulfo-4-nitrochlorobenzene, 2-carboxy-4-nitrochlorobenzene, 2-(β-hydroxyethylsulfonyl)-4-nitrochlorobenzene, 2-[N,N-di-(β-hydroxyethyl)-sulfamoyl]-4-nitrochlorobenzene, 2-[N-(β-hydroxyethyl)-sulfamoyl]-4-nitrochlorobenzene, 2-[N-(β-sulfoethyl)-sulfamoyl]-4-nitrochlorobenzene, 2-[N-methyl-N-(β-sulfoethyl)sulfamoyl]-4-nitrochlorobenzene, 2-[N-(4'-β-hydroxyethylsulfonyl-2'-sulfophenyl)-ethylsulfamoyl]-4-nitrochlorobenzene, 2-(N-phenethyl)-sulfamoyl-4-nitrochlorobenzene, 2-phenylsulfamoyl-4-nitrochlorobenzene, 2-[N-(3'-β-hydroxyethylsulfonyl-4'-β-hydroxyethylaminophenyl)sulfamoyl]-4-nitrochlorobenzene, 2-[N-(3'-β-hydroxyethylsulfonyl-4-methoxyphenyl)-sulfamoyl]-4-nitrochlorobenzene, 2-[N-β-(β'-hydroxyethylsulfonyl)-ethylsulfamoyl]-4-nitrochlorobenzene, 2-[N-(phenylsulfonyl)sulfamoyl]-4-nitrochlorobenzene and 2-[N-(methylsulfonyl)sulfamoyl]-4-nitrochlorobenzene.

Starting compounds of the general formula (7) indicated and defined above in which n=1 are not yet known in the literature; they can, however, be prepared analagously to the procedures described in the literature, for example by reacting 4-(β-hydroxyethylsulfonyl)-2-nitrochlorobenzene, which is known from Example 5 of German Patent No. 859,462, with an amine of the general formula A—B—W—NH$_2$ in which B and W have the abovementioned meaning and A denotes a hydrogen atom or an acyl radical, such as an alkanoyl radical having 2 to 5 carbon atoms, for example the acetyl radical, or the benzoyl radical, with the elimination of hydrogen chloride, and then reducing the nitro group in the compound thus obtained, and, in the aniline compound obtained therefrom of the general formula

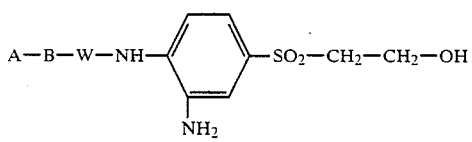

in which A, B and W have the meanings mentioned above, diazotizing the amino group thereof in a manner customary per se, in the course of which cyclization to give the triazole takes place simultaneously. If the benzotriazole compound thus formed still contains the acyl radical A, this can subsequently be eliminated by hydrolysis in a customary manner.

Thus the synthesis of the starting compounds of the general formula (7) can be carried out analogously to this by reacting a compound of the general formula (9)

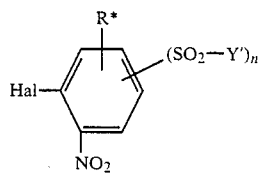

in which R*, Y' and n have the meanings mentioned above and Hal represents a fluorine or bromine atom, with a compound of the general formula A—B—W—NH$_2$ in which A, B and W have the meanings mentioned above and B is preferably the group NH, in a solvent suitable for these reactants and in the presence of an acid-binding agent, at a temperature between 30° and 120° C., preferably between 70° and 90° C.

Examples of starting compounds corresponding to the formula A—B—W—NH$_2$ are 1,2-diaminoethane, 1,3-diaminopropane, 1,4-diaminobutane, 1,5-diaminopentane, 1,6-diaminohexane, 1,2-diaminopropane, 1,2-diaminobutane, 1,3-diaminobutane, the N-acyl compounds, such as the N-acetyl and N-benzoyl compounds, of 1-amino-3-methylaminopropane, 1,3-diamino-2-methylpropane, 1,3-diamino-2-hydroxypropane, 1,5-diamino-2-carboxypentane, 1,3-diamino-2-phenylpropane or its derivative which is sulfosubstituted in the benzene radical, and also compounds corresponding to a general formula (a*), (b*), (c*) and (d*)

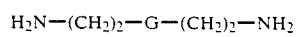  (a*)

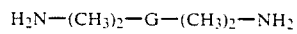  (b*)

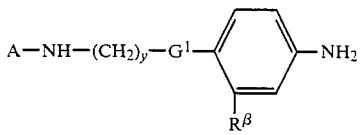  (c*)

H$_2$N—(CH$_2$—CH$_2$—NH)$_r$—CH$_2$—CH$_2$—NH$_2$   (d*)

in which

G denotes an oxygen atom, a sulfur atom, a sulfonyl group or a group of formula —NH—, —N(CH$_3$)— or —N(COCH$_3$)—, R$^\beta$ represents a hydrogen atom or a sulfo group, A has the meaning mentioned above, r is the number 2, 3 or 4, G$^1$ represents the group —NH— or an oxygen atom and y denotes the number 2 or 3, and also 1,3-cyclohexylenediamine, 1,4-cyclohexylenediamine, bis-(4-aminocyclohex-1-yl)-methane, 1,8-di(aminomethyl)-naphthalene, 1,4-di-(aminomethyl)-benzene, 1,3-di-(aminomethyl)-benzene, N,N'-bis-(β-aminoethyl)-1,4-piperidine, 1,4-phenylenediamine, 1,3-phenylenediamine, 4-aminobenzylamine, 4-aminophenethylamine and the corresponding N-monoacyl derivatives of such compounds, of which 1,2-diaminoethane, 1,3-diaminopropane, 1,4-diaminobutane and 1,2-diaminopropane are preferred.

Examples of solvents suitable for the reaction between the halogenonitrobenzenes and the amino compounds are water, alkanols having 1 to 4 carbon atoms, dioxane, toluene, the xylenes, chlorobenzene, o-dichlorobenzene, m-dichlorobenzene, dimethylformamide and N-methylpyrrolidone. The amine itself in excess can also be used as the solvent.

The nitro compound thus synthesized of the general formula (10)

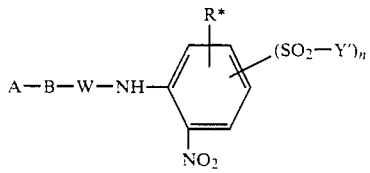

in which A, B, R*, W, Y' and n have the meanings mentioned above can be isolated in a manner customary per se, for example by crystallization from this reaction mixture or by removing the solvent or excess amine by distillation or by acidification and filtration.

The subsequent reduction of the nitro group in the nitro compound (10) to the amino group can be carried out in a manner known per se, for example by catalytic hydrogenation with hydrogen over palladium, platinum or Raney nickel at a temperature between 50° and 110° C. and under an elevated pressure or by reduction by the Béchamp method using iron in an acid medium, for example iron in ethanol/glacial acetic acid. The reduction can be carried out in a solvent suitable for this purpose, such as water, methanol or ethanol or a mixture thereof.

The amino compound present in the hydrogenation mixture can—after prior removal of catalysts or metallic reducing agents—be diazotized directly, without intermediate isolation, with simultaneous cyclization to give the triazole. The diazotization is carried out by a procedure customary per se, for example using sodium nitrite in a hydrochloric acid medium at a temperature between −5° C. and +15° C. An acylamino group which may be present in the resulting benzotriazole compound can be hydrolysed by a customary procedure, for example in an aqueous medium at a pH higher than 12 and at a temperature of 90° to 100° C., to give the amino group and hence the compound of the general formula (7).

The following are examples of starting compounds of the general formula (7) indicated and defined above which contain the fiber-reactive radical of the vinyl sulfone series or which represent the β-hydroxyethylsulfonyl derivative thereof: β-[5-(β-hydroxyethylsulfonyl)benzotriazol-1-yl]-ethylamine, γ-[5-β-hydroxyethylsulfonyl)-benzotriazol-1-yl]-n-propylamine, the ω-[5-β-hydroxyethylsulfonyl)-benzotriazol-1-yl]-C$_4$–C$_6$-n-alkylamines, β-[5-(β-hydroxyethylsulfonyl)-benzotriazol-1-yl]-ethanol, the ω-[5-(β-hydroxyethylsulfonyl)-benzotriazol-1-yl]-C$_3$–C$_6$-n-alkanols, β-[5-(β-hydroxyethylsulfonyl)-benzotriazol-1-yl]-n-propylamine, 4-[5′-(β-hydroxyethylsulfonyl)-benzotriazol-1′-yl]-cyclohexylamine, β-{4-[5′(β-hydroxyethylsulfonyl)-benzotriazol-1′-yl]-phenylamino}-ethylamine, β-{4-[5′-(β-hydroxyethylsulfonyl)-benzotriazol-1′-yl]-phenylamino}-ethanol, 4-[5′-(β-hydroxyethylsulfonyl)-benzotriazol-1′-yl]phenethylamine and the other benzotriazole compounds or β-hydroxyethylsulfonyl derivatives thereof which are evident in large numbers from the examples.

Large numbers of the benzoquinones of the general formula (5) used as the starting compounds are known in the literature. The following are examples of compounds of this type: 1,4-benzoquinone, 2-methyl-1,4-benzoquinone, 2-ethyl-1,4-benzoquinone, 2-n-propyl-1,4-benzoquinone, 2-isopropyl-1,4-benzoquinone, 2-(β-ethoxyethyl)-1,4-benzoquinone, 2-phenyl-1,4-benzoquinone, 2-(4′-methylphenyl)-1,4-benzoquinone, 2-(4′-methoxyphenyl)-1,4-benzoquinone, 2-(3′-chlorophenyl)-1,4-benzoquinone, 2-(4′-nitrophenyl)-1,4-benzoquinone, 2,5-dimethyl-1,4-benzoquinone, 2-methyl-5-ethyl-1,4-benzoquinone, 2-methyl-3-chloro-1,4-benzoquinone, 2-methyl-6-chloro-1,4-benzoquinone, 2-methyl-3,5-dichloro-1,4-benzoquinone, 2-methyl-3,5,6-tribromo-1,4-benzoquinone, 2-(4′-methylphenoxy)-3,6-dibromo-1,4-benzoquinone, 2-(3′-methylphenoxy)-3,6-dibromo-1,4-benzoquinone, 2-methyl-3,5,6-trichloro-1,4-benzoquinone, 2-methyl-3-chloro-5-bromo-1,4-benzoquinone, 2-methyl-3,6-dichloro-1,4-benzoquinone, 2-methyl-3,6-dichloro-5-bromo-1,4-benzoquinone, 2-phenyl-3,6-dichloro-1,4-benzoquinone, 2-(4′-methoxyphenyl)-3,6-dichloro-1,4-benzoquinone, 2-(4′-chlorophenyl)-3,6-dichloro-1,4-benzoquinone, 2-(4′-nitrophenyl)-3,6-dichloro-1,4-benzoquinone, 2-(4′-nitrophenyl)-3,5,6-trichloro-1,4-benzoquinone, 2,5-dimethyl-3,6-dibromo-1,4-benzoquinone, 2,5-dimethyl-3-chloro-1,4-benzoquinone, 2-methyl-5-n-propyl-6-bromo-1,4-benzoquinone, 2-methyl-5-isopropyl-3-chloro-1,4-benzoquinone, 2-methyl-5-isopropyl-6-bromo-1,4-benzoquinone, 2-(2′-chlorophenyl)-3,5,7-tribromo-1,4-benzoquinone, 2-methyl-3-methoxy-1,4-benzoquinone, 2,3,5,6-tetramethoxy-1,4-benzoquinone, 2,3,5,6-tetraphenoxy-1,4-benzoquinone, 2,3,5,6-tetra-(4′-methylphenoxy)-1,4-benzoquinone, 2,3,5,6-tetra-(4′-methoxyphenyl)-1,4-benzoquinone, 2,3,5,6-tetra-(4′-chlorophenoxy)-1,4-benzoquinone, 2,3,5,6-tetra-4-(3′-methyl-4′-chlorophenoxy)-1,4-benzoquinone, 2-ethyl-3,6-dimethoxy-1,4-benzoquinone, 2-chloro-3,6-dimethoxy-1,4-benzoquinone, 2,3,5-trimethoxy-1,4-benzoquinone, 2,5-dimethyl-3,6-dimethoxy-1,4-benzoquinone, 2,5-dimethyl-3,6-dimethoxy-1,4-benzoquinone, 2-methyl-3,6-dimethoxy-1,4-benzoquinone, 2-methyl-5,6-dimethoxy-1,4-benzoquinone, 2-ethyl-3,6-dimethoxy-1,4-benzoquinone, 2-chloro-3-n-propyl-5-methoxy-1,4-benzoquinone and 2-chloro-3,5-dimethoxy-1,4-benzoquinone, 2,3,5,6-tetrafluoro-1,4-benzoquinone and, preferably, 2,3,5,6-tetrabromo-1,4-benzoquinone and, in particular, 2,3,5,6-tetrachloro-1,4-benzoquinone.

The separation and isolation of the compounds of the general formula (1) prepared in accordance with the invention, from the synthesis solutions, can be effected by methods which are generally known, for example either by precipitation from the reaction medium by means of electrolytes, such as, for example, sodium chloride or potassium chloride, or by evaporating, for example, spray drying, the reaction solution, it being possible to add a buffer substance to this reaction solution.

The compounds, according to the invention, of the general formula (1) have fiber-reactive properties and possess valuable properties as dyestuffs. They can therefore be used for dyeing (including printing) natural, regenerated or synthetic materials containing hydroxy groups and/or carboxamide groups, for example in the form of sheet-like structures, such as paper and leather, or, in bulk, polyamide or polyurethane, but especially materials of this type in fiber form, such as cellulose fiber materials, silk, wool and synthetic polyamide and polyurethane fibers. The solutions obtained in the synthesis of the compounds according to the invention can also be applied, without further treatment, as a liquid preparation, for tinctorial use, if appropriate after the addition of a buffer substance and if appropriate after being concentrated.

In accordance with use according to the invention, the compounds, according to the invention, of the formula (1) can be applied to and fixed on the substrates mentioned, in particular on the fiber materials mentioned, by the techniques of application which are known for water-soluble, in particular fiber-reactive, dyestuffs, for example by applying the dioxazine compound of the general formula (1) in a dissolved form to the substrate or introducing it into the substrate, and fixing it on or in this substrate, if appropriate by the application of heat and/or, if appropriate, by the action of an agent having an alkaline action. Large numbers of such dyeing and fixing methods are described in the literature.

The present invention therefore also relates to the use of the compounds, according to the invention, of the general formula (1) for dyeing (including printing) materials containing hydroxy and/or carboxamide groups and to processes for their use on these substrates. The materials are preferably used in the form of fiber materials, in particular in the form of textile fibers, such as yarns, wound packages and fabrics. In this regard it is possible to use procedures analagous to known procedures for applying and fixing fiber-reactive dyestuffs.

The dyeings and prints produced using compounds, according to the invention, of the general formula (1) are distinguished by clear, mainly blue, color shades. In particular, the dyeings and prints on cellulose fiber materials have a very high depth of color and also very good fastness properties to light, including good fastness properties to light under wet conditions and in perspiration, also good fastness properties to hypochlorite bleaching and to chlorinated water and also excellent fastness properties to wet processing, such as, for example, good to very good fastness properties to washing at 60° to 95° C., even in the presence of perborates, fastness properties to cross-dyeing and perspiration, milling under acid and alkaline conditions, fastness properties to alkali, acid, water and sea water, and also good fastness to pleating, good fastness to hot ironing which is adjusted to a value of 5 with sodium carbonate, and the compound is salted out by means of sodium chloride, if necessary after clarifying the solution beforehand in a customary manner.

The triphendioxazine compound according to the invention can also be obtained in the form of its sodium salt by evaporating or spray drying the clarified synthesis solution. Expressed in the form of the free acid, it has the probable formula

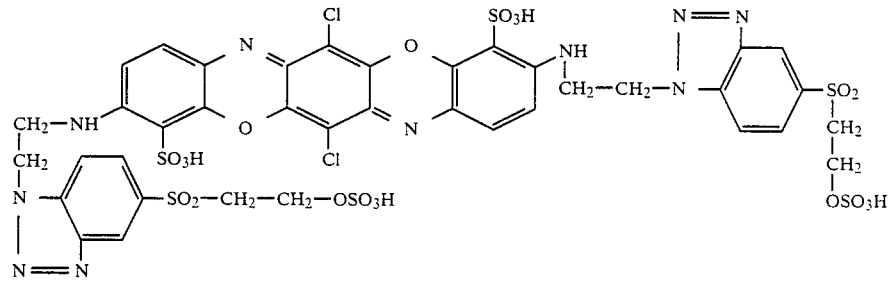

and fastness to rubbing. They also possess good fastness to wet storage and very good resistance to acid fading when moist, dyed material still containing acetic acid is stored. The dyeings are also stable to the customary synthetic resin finishes. Some of the compounds according to the invention (dyestuffs) are comparable with the fiber-reactive anthraquinone dyestuffs in clearness of color shade and in important fastness properties.

The Examples below serve to illustrate the invention. The parts are parts by weight and the percentages are percentages by weight, unless a note is made to the contrary. Parts by weight stand in the same relation to parts by volume as kilograms to liters.

EXAMPLE 1

(a) 441 parts of the compound of the formula (each of the sulfo groups can also be attached in the other ortho-position relative to the benzotriazolylethylamino group, but are more probably in the position indicated in the above formula).

This compound according to the invention possesses good fiber-reactive properties as a dyestuff. It dyes the materials mentioned in the description, in particular cellulose fiber materials, such as cotton, by the procedures which are customary and known in the art for the application and fixation of fiber-reactive dyestuffs, in deep, clear, reddish-tinged blue shades (corresponding to the color coefficient 13 of the Color Index Hue Indication Chart) having good fastness properties, such as, in particular, good fastness to light in the dry or moist, such as moistened with drinking water, dyeing, good fastness to light in alkaline perspiration, fastness to chlo-

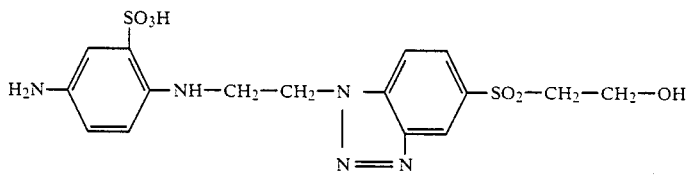

are dissolved in 2,000 parts of water at pH 6° and 60° C. 124 parts of chloranil are introduced, the pH being maintained at a value of 6.5 by means of about 90 parts of sodium bicarbonate and the reaction temperature being maintained at about 65° C. The mixture is stirred for a further 6 hours, and the reaction product is then clarified at about 65° C., precipitated by means of little sodium chloride, filtered off with suction, washed with 1,000 parts of 10% strength aqueous sodium chloride solution and dried at 70° C. under reduced pressure.

(b) 105 parts of the product obtained under (a) are introduced into 750 parts of 7% strength oleum at a temperature between 20° and 25° C. The reaction mixture is then stirred for about another 3 hours at this temperature; 48 parts of sodium peroxodisulfate are then introduced at such a rate that the reaction temperature can be kept at 20° to 25° C. The mixture is stirred for a further 10 hours at this temperature, and is then run onto ice, and the compound, according to the invention, which has been precipitated is filtered off and redissolved in about 1,000 parts of water the pH of rinated water, fastness to hypochlorite, fastness to alkaline perspiration, fastness to washing, even in the presence of perborates, fastness to wet storage and resistance to acid fading. In aqueous solution it exhibits an absorption maximum at 612 nm in the visible range.

(c) The 4-[β-(5'-β-hydroxyethylsulfonylbenzotriazole-1'-yl)-ethylamino]-3-sulfoaniline employed under (a) can, for example, be prepared as follows:

259 parts of the sodium salt of 5-nitro-2-chlorobenzenesulfonic acid are added to a mixture, preheated to 40° C., of 270 parts of 5-(β-hydroxyethylsulfonyl)-1-(β-aminoethyl)-benzotriazole in 1,000 parts of water and 500 parts of triethanolamine. The mixture is heated to 100° to 100° C. in the course of two hours, part of the water distilling off. The mixture is stirred for a further ten hours at 115° to 120° C. to achieve quantitative reaction, and 3,000 parts of water are then added at 100° C., and the solution is clarified at 80° to 90° C. On cooling, the sodium salt of 4-[β-(5'-β'-hydroxyethylsulfonylbenzotriazol-1'-yl)-ethylamino]-3-sulfonitrobenzene crystallizes out from the aqueous medium in a high yield and high purity.

The nitro compound exhibits the following data in $^1$H-NMR analysis (in D$_6$-DMSO using TMS as internal standard): $\delta = 3.5$ ppm (m, 2H); 3.64 ppm (t, 2H); 3.95 ppm (m, 2H); 4.82 ppm (t, OH); 5.0 ppm (t, 2H); 6.69 ppm (d, 1H); 7.57 ppm (t, NH); 7.95 ppm (m, 2H); 8.16 ppm (m, 1H); 8.3 ppm (d, 1H); 8,57 ppm (d, 1H).

(d) The nitro compound from (c) is reduced to the aniline compound by catalytic hydrogenation, by dissolving 236 parts of the nitro compound in 1,000 parts of water and hydrogenating it in the presence of a Pd-on-charcoal catalyst in an autoclave at a temperature of up to 100° C. and a hydrogen pressure of 50 bar. The catalyst is then filtered off and the filtrate is cooled and acidified. The aniline compound crystallizes out therefrom in a good yield and high purity. $^1$H-NMR analysis gives the following data: $\delta = 3.4$–3.9 ppm (m, 6H); 4.96 ppm (m, 2H, OH, NH); 6.68 ppm (d, 1H); 7.1 ppm (dd, 1H); 7.52 ppm (d, 1H); 7.95 ppm (dd, 1H); 8.15 ppm (d, 1H); 8.58 ppm (m, 1H); 9.7 ppm (broad NH$_3^+$).

The hydrogenation solution can also be used without further treatment for reaction of (a).

(e) The benzotriazolylethylamino compound employed under (c) can, for example, be prepared as follows:

260 parts of $\beta$-[4-($\beta$-hydroxyethylsulfonyl)-2-aminophenylamino]-ethylamine are diazotized in a customary manner in about 1,800 parts of an aqueous solution of hydrochloric acid at 0° to 5° C. by means of an aqueous solution of sodium nitrite. Cyclization takes place immediately and quantitatively. The solution can be employed without further treatment in (c).

A sample isolated exhibits the following $^1$H-NMR analytical data (in D$_6$-DMSO using TMS as internal standard): $\delta = 3.06$ ppm (t, 2H); 3.54 ppm (m, 2H); 3.7 ppm (m, 2H); 4.72 ppm (t, 2H); 8.0 ppm (dd, 1H); 8.16 ppm (dd, 1H); 8.6 ppm (m, 1H); mobile protons (OH, NH$_2$).

(f) The 4-hydroxyethylsulfonyl-2-aminophenylaminoethylamine compound employed under (e) can, for example, be obtained as follows:

530 parts of 4-($\beta$-hydroxyethylsulfonyl)-2-nitrochlorobenzene are introduced slowly, at 70° to 80° C., into 620 parts of ethylenediamine. After a quantitative reaction has taken place, the resulting product is stirred thoroughly into water and is filtered off with suction. The nitro compound is obtained in a good yield and high purity (melting point 146°/147° C.).

In $^1$H-NMR analysis (in D$_6$-DMSO using TMS as internal standard) it gives the following data: $\delta = 2.83$ ppm (t, 2H); 3.44 ppm (m, 2H); 3.7 ppm (m, 2H); 7.27 ppm (d, 1H); 7.9 ppm (dd, 1H); 8.49 ppm (d, 1H); mobile protons at 1.7 ppm (NH$_2$), 4.8 ppm (OH) and 8.8 ppm (NH).

(g) The nitro compound from (f) is reduced to the aniline compound by hydrogenating 290 parts of the nitro compound in 1,200 parts of water in the presence of a Pd-on-charcoal catalyst in an autoclave at a temperature of up to 100° C. and a hydrogen pressure of 50 bar. The catalyst is then filtered off and the filtrate can be processed further in (e) without further treatment.

A sample isolated (melting point 169°–172° C.) gives the following data in $^1$H-NMR analysis (in D$_6$-DMSO using TMS as internal standard): $\delta = 2.84$ ppm (t, 2H); 3.2 ppm (m, 4H); 3.6 ppm (m, 2H); 6.53 ppm (dd, 1H); 6.96 ppm (d, 1H); 7.0 ppm (dd, 1H); mobile protons at 4–5 ppm (NH$_2$, OH) and 5.45 ppm (NH).

EXAMPLE 2

(a) 455 parts of the compound of the formula

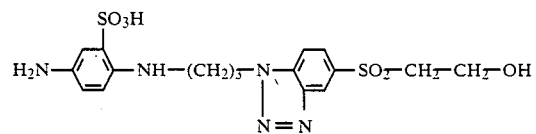

are dissolved in 2,000 parts of water at pH 6 and 60° C. 124 parts of chloranil are introduced, the pH being kept at a value of 6.5 by means of about 90 parts of sodium bicarbonate and the reaction temperature being kept at about 65° C. The mixture is stirred for a further six hours, and the reaction product is then clarified at about 25° C., precipitated by means of a little sodium chloride, filtered off with suction, washed with 1,000 parts of 10% strength aqueous sodium chloride solution and dried at 70° C. under reduced pressure.

(b) 108 parts of the product obtained under (a) are introduced into 750 parts of 13% strength oleum at a temperature between 20° and 25° C. The reaction mixture is then stirred for about a further three hours at this temperature; 48 parts of sodium peroxodisulfate are then introduced at such a rate that the reaction temperature can be kept at 20° to 25° C. The mixture is stirred for a further ten hours at this temperature and is then run onto ice, and the compound according to the invention which has been precipitated is filtered off and redissolved in about 1,000 parts of water the pH of which is adjusted to a value of 5 with sodium carbonate, and the compound is salted out with sodium chloride, if necessary after clarifying the solution beforehand in a customary manner.

The triphendioxazine compound according to the invention can also be obtained in the form of its sodium salt by evaporating or spray drying the clarified synthesis solution. Expressed in the form of the free acid, it has the probable formula

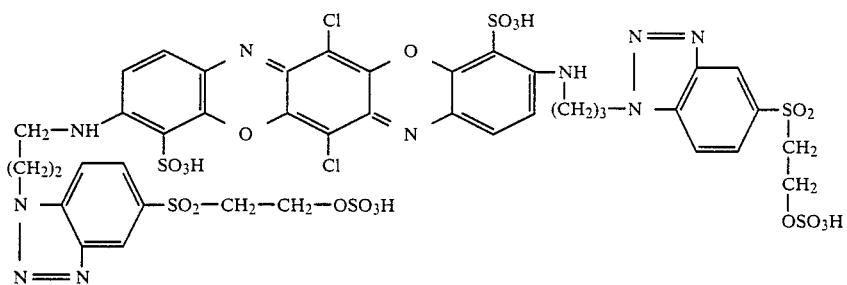

(each of the sulfo groups can also be attached in the other ortho-position relative to the benzotriazolyl-propylamino group, but is more probably in the position indicated in the above formula).

This compound according to the invention possesses good fiber-reactive properties as a dyestuff. It dyes the materials mentioned in the description, in particular cellulose fiber materials, such as cotton, by the procedures customary and known in the art for the application and fixation of fiber-reactive dyestuffs, in deep, clear, reddish-tinged blue shades (corresponding to the color coefficient 13 of the Color Index Hue Indication Chart) having good fastness properties, such as, in particular, good fastness to light in the dry or moist, such as moistened with drinking water, dyeing, good fastness to light in alkaline perspiration, fastness to chlorinated water, fastness to hypochlorite, fastness to alkaline perspiration, fastness to washing, even in the presence of perborates, fastness to wet storage and resistance to acid fading. In aqueous solution it exhibits an absorption maximum of 618 mm in the visible range.

(c) The 4-[γ-(5'-β-hydroxyethylsulfonylbenzotriazol-1'-yl)-propylamino]-3-sulfoaniline employed under (a) can, for example, be prepared as follows: 259 parts of the sodium salt of 5-nitro-2-chlorobenzenesulfonic acid are added to a mixture, preheated to 40° C., of 285 parts of 5-(β-hydroxyethylsulfonyl)-1-(γ-aminopropyl)benzotriazole in 1,000 parts of water and 500 parts of triethanolamine. The mixture is heated to 100° to 110° C. in the course of two hours, part of the water distilling off. Stirring is continued for a further ten hours at 115° to 120° C. to achieve a quantitative reaction, and 3000 parts of water are then added at 100° C., and the solution is clarified at 80° to 90° C. On cooling, the sodium salt of 4-[γ-(5'-β'-hydroxyethylsulfonylbenzotriazol-1'-yl)-propylamino]-3-sulfonitrobenzene crystallizes out from the aqueous medium in a high yield and purity. The nitro compound gives the following data in $^1$H-NMR analysis (in $D_6$-DMSO using TMS as internal standard): δ=2.25 ppm (m, 2H); 3.32 ppm (m, 2H); 3.54 ppm (m, 2H); 3.66 ppm (m, 2H); 4.9 ppm (m, OH, 2H); 6.69 ppm (d, 1H); 7.47 ppm (t, NH); 8.0 ppm (m, 2H); 8.20 ppm (m, 1H); 8.37 ppm (d, 1H); 8.62 ppm (d, 1H).

(d) The nitro compound from (c) can be hydrogenated catalytically analagously to Example 1(d). It gives the following $^1$H-NMR data: δ=2.2 ppm (m, 2H); 3.14 ppm (t, 2H); 3.56 ppm (t, 2H); 3.7 ppm (t, 2H); 4.9 ppm (t, 2H); 6.6 ppm (d, 1H); 7.05 ppm (dd, 1H); 7.54 ppm (d, 1H); 7.95 ppm (dd, 1H); 8.17 ppm (d, 1H); 8.59 ppm (d, 1H); 9.5 ppm (broad $NH_3^+$); mobile protons (OH, NH) at approx. 5 ppm.

The starting compounds employed in (c) for the compound of (c) can be prepared analagously to Examples 1(e) to 1(g).

EXAMPLES 3 TO 81

Further triphendioxazine compounds according to the invention corresponding to the general formula (1A)

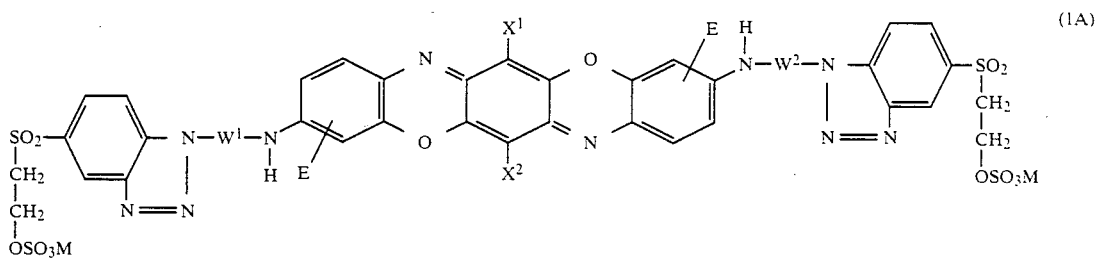

(in which M has the meaning indicated in the description) are described by means of their radicals in the Tabular Examples below (in these, the radical $W^2$ represents in each case the group, having a "mirror image" structure, of the radical $W^1$ shown). They can be prepared in a manner according to the invention, for example analagously to the procedures of the above Examples, by reacting a 1,4-benzoquinone compound corresponding to the general formula (5) and shown in the appropriate Tabular Example, with a compound of the general formula (4A)

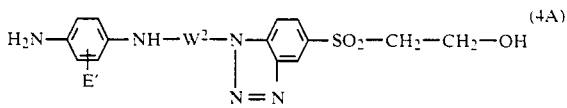

(in which E' is the hydroxy derivative of E, if E contains a sulfato group), and subsequent sulfation and cyclization. These triphendioxazine compounds according to the invention also possess very good fiber-reactive properties as dyestuffs and afford, on the materials mentioned in the description, such as, in particular, cellulose fiber materials, deep, fast dyeings having the color shade on cotton indicated in the appropriate Tabular Example (this has the color coefficient indicated in parentheses of the Color Index Hue Indication Chart). The values given in brackets represent the absorption maxima in the visible range of the dyes, determined in aqueous solution and in nm.

| | | | Compound corresponding to formula (1A) | | | | |
|---|---|---|---|---|---|---|---|
| Ex. | Radical E | Radical W² | | X¹ is ... | X² is ... | Compound (5) = ... 1,4-benzo-quinone | Color shade |
| 3 | Sulfo | 1,2-Ethylene | | Bromine | Bromine | 2,3,5,6-Tetra-bromo-... | Reddish-tinged blue (13) [612] |
| 4 | Sulfo | " | | Methyl | Methyl | 2,5-Dimethyl-3,6-dichloro-... | Reddish-tinged blue (13) [612] |
| 5 | Sulfo | " | | Methyl | Chlorine | 2-Methyl-3,5,6-trichloro-... | Reddish-tinged blue (13) [612] |
| 6 | Sulfo | " | | Methoxy | Methoxy | 2,3,5,6-Tetra-methoxy-... | Reddish-tinged blue (13) [612] |
| 7 | Sulfo | 1,3-Propylene | | Chlorine | Chlorine | 2,3,5,6-Tetra-chloro-... | Reddish-tinged blue (13) [618] |
| 8 | Sulfo | " | | Bromine | Bromine | 2,3,5,6-Tetra-bromo-... | Reddish-tinged blue (13) [618] |
| 9 | Sulfo | " | | Methyl | Methyl | 2,5-Dimethyl-3,6-dichloro-... | Reddish-tinged blue (13) [618] |
| 10 | Sulfo | " | | Methyl | Chlorine | 2-Methyl-3,5,6-trichloro-... | Reddish-tinged blue (13) [618] |
| 11 | Sulfo | —CH(CH₃)—CH₂— | | Chlorine | Chlorine | 2,3,5,6-Tetra-chloro-... | Reddish-tinged blue (13) [614] |
| 12 | Suflo | " | | Bromine | Bromine | 2,3,5,6-Tetra-bromo-... | Reddish-tinged blue (13) [614] |
| 13 | Sulfo | 1,4-Butylene | | Chlorine | Chlorine | 2,3,5,6-Tetra-chloro-... | Reddish-tinged blue (13) [614] |
| 14 | Sulfo | 1,6-Hexylene | | Chlorine | Chlorine | 2,3,5,6-Tetra-chloro-... | Reddish-tinged blue (13) [614] |
| 15 | Sulfo | 2-Sulfato-1,3-propylene | | Chlorine | Chlorine | 2,3,5,6-Tetra-chloro-... | Reddish-tinged blue (13) [614] |
| 16 | Sulfo | 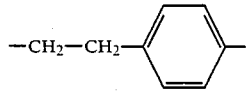 | | Chlorine | Chlorine | 2,3,5,6-Tetra-chloro-... | Reddish-tinged blue (13) |
| 17 | Sulfo | 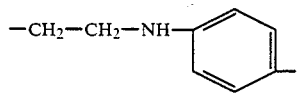 | | Chlorine | Chlorine | 2,3,5,6-Tetra-chloro-... | Reddish-tinged blue (13) |
| 18 | Sulfo | 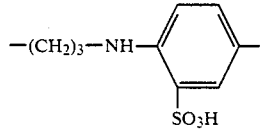 | | Chlorine | Chlorine | 2,3,5,6-Tetra-chloro-... | Reddish-tinged blue (13) |
| 19 | Sulfo | 1,4-Phenylene | | Chlorine | Chlorine | 2,3,5,6-Tetra-chloro-... | Greenish-tinged blue (15) |
| 20 | Sulfo | 1,5-Pentylene | | Chlorine | Chlorine | 2,3,5,6-Tetra-chloro-... | Reddish-tinged blue (13) |
| 21 | Sulfo | —CH(C₂H₅)—CH₂— | | Chlorine | Chlorine | 2,3,5,6-Tetra-chloro-... | Reddish-tinged blue (13) |
| 22 | Sulfo | —CH—CH₂—CH₂— <br>     | <br>    CH₃ | | Chlorine | Chlorine | 2,3,5,6-Tetra-chloro-... | Reddish-tinged blue (13) |
| 23 | Sulfo | 2-Methyl-1,3-propylene | | Chlorine | Chlorine | 2,3,5,6-Tetra-blue (13) | Reddish-tinged |
| 24 | Sulfo | 2-Methoxy-1,3-propylene | | Chlorine | Chlorine | 2,3,5,6-Tetra-chloro-... | Reddish-tinged blue (13) |
| 25 | Sulfo | —(CH₂)₃—O—(CH₂)₂ <br>            | <br>         O—(CH₂)₃— | | Chlorine | Chlorine | 2,3,5,6-Tetra-chloro-... | Reddish-tinged blue (13) |
| 26 | Sulfo | —(CH₂)₂—SO₂—(CH₂)₂— | | Chlorine | Chlorine | 2,3,5,6-Tetra-chloro-... | Reddish-tinged blue (13) |

-continued

| | | Compound corresponding to formula (1A) | | | Compound (5) = ... 1,4-benzo- | |
|---|---|---|---|---|---|---|
| Ex. | Radical E | Radical $W^2$ | $X^1$ is ... | $X^2$ is ... | quinone | Color shade |
| 27 | Sulfo | $-CH_2-\text{C}_6H_4-$ 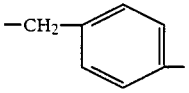 | Chlorine | Chlorine | 2,3,5,6-Tetra-chloro-... | Reddish-tinged blue (13) |
| 28 | Sulfo | $-(CH_2)_2-N(CH_3)-(CH_2)_2-$ | Chlorine | Chlorine | 2,3,5,6-Tetra-chloro-... | Reddish-tinged blue (13) |
| 29 | Sulfo | $-CH_2-CH_2-O-\text{C}_6H_4-$ 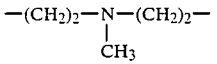 | Chlorine | Chlorine | 2,3,5,6-Tetra-chloro-... | Reddish-tinged blue (13) |
| 30 | Sulfo | $-CH(COOH)-(CH_2)_4-$ | Chlorine | Chlorine | 2,3,5,6-Tetra-chloro-... | Reddish-tinged blue (13) |
| 31 | Sulfo | $-(CH_2)_3-NH-(CH_2)_3-$ | Chlorine | Chlorine | 2,3,5,6-Tetra-chloro-... | Reddish-tinged blue (13) |
| 32 | Sulfo | 2-methyl-4-sulfo-phenylene 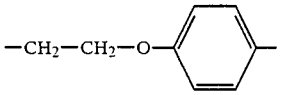 | Chlorine | Chlorine | 2,3,5,6-Tetra-chloro-... | Greenish-tinged blue (15) |
| 33 | Carboxy | 1,2-Ethylene | Chlorine | Chlorine | 2,3,5,6-Tetra-chloro-... | Reddish-tinged blue (13) |
| 34 | Carboxy | 1,2-Ethylene | Bromine | Bromine | 2,3,5,6-Tetra-bromo-... | Reddish-tinged blue (13) |
| 35 | Carboxy | " | Methyl | Chlorine | 2-Methyl-3,5,6-trichloro-... | Reddish-tinged blue (13) |
| 36 | Carboxy | " | Methoxy | Methoxy | 2,3,5,6-Tetra-methoxy-... | Reddish-tinged blue (13) |
| 37 | Carboxy | 1,3-Propylene | Chlorine | Chlorine | 2,3,5,6-Tetra-chloro-... | Reddish-tinged blue (13) |
| 38 | Carboxy | " | Bromine | Bromine | 2,3,5,6-Tetra-bromo-... | Reddish-tinged blue (13) |
| 39 | Carboxy | " | Methyl | Methyl | 2,5-Dimethyl-3,6-dichloro-... | Reddish-tinged blue (13) |
| 40 | Carboxy | " | Methyl | Chlorine | 2-Methyl-3,5,6-trichloro-... | Reddish-tinged blue (13) |
| 41 | Carboxy | $-CH(CH_3)-CH_2-$ | Chlorine | Chlorine | 2,3,5,6-Tetra-chloro-... | Reddish-tinged blue (13) |
| 42 | Carboxy | " | Bromine | Bromine | 2,3,5,6-Tetra-bromo-... | Reddish-tinged blue (13) |
| 43 | Carboxy | 2-(4'-Sulfophenyl)-1,3-propylene | Chlorine | Chlorine | 2,3,5,6-Tetra-chloro-... | Reddish-tinged blue (13) |
| 44 | Carboxy | $-CH_2-CH_2-O-CH_2-CH_2-$ | Chlorine | Chlorine | 2,3,5,6-Tetra-chloro-... | Reddish-tinged blue (13) |
| 45 | Carboxy | 2-Sulfato-1,3-propylene | Chlorine | Chlorine | 2,3,5,6-Tetra-chloro-... | Reddish-tinged blue (13) |
| 46 | Carboxy | $-CH_2-CH_2-\text{C}_6H_4-$ 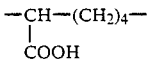 | Chlorine | Chlorine | 2,3,5,6-Tetra-chloro-... | Reddish-tinged blue (13) |
| 47 | Carboxy | $-(CH_2)_2-NH-$(2-sulfophenyl)- 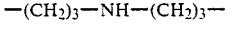 | Chlorine | Chlorine | 2,3,5,6-Tetra-chloro-... | Reddish-tinged blue (13) |
| 48 | Carboxy | $-(CH_2)_3-NH-\text{C}_6H_4-$ 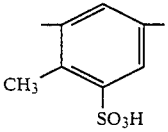 | Chlorine | Chlorine | 2,3,5,6-Tetra-chloro-... | Reddish-tinged blue (13) |

-continued

Compound corresponding to formula (1A)

| Ex. | Radical E | Radical W² | X¹ is... | X² is... | Compound (5) = ...1,4-benzo-quinone | Color shade |
|---|---|---|---|---|---|---|
| 49 | Carboxy | Sulfophen-1,4-ylene | Chlorine | Chlorine | 2,3,5,6-Tetra-chloro-... | Greenish-tinged blue (14) |
| 50 | N,N—Di-(β-sulfato-ethyl)-sulfamoyl | 1,2-Ethylene | Bromine | Bromine | 2,3,5,6-Tetra-bromo-... | Reddish-tinged blue (13) |
| 51 | N,N—Di-(β-sulfato-ethyl)-sulfamoyl | " | Chlorine | Chlorine | 2,3,5,6-Tetra-chloro-... | Reddish-tinged blue (13) |
| 52 | N,N—Di-(β-sulfato-ethyl)-sulfamoyl | " | Methyl | Chlorine | 2-Methyl-3,5,6-trichloro-... | Reddish-tinged blue (13) |
| 53 | N,N—Di-(β-sulfato-ethyl)-sulfamoyl | " | Methoxy | Methoxy | 2,3,5,6-Tetra-methoxy-... | Reddish-tinged blue (13) |
| 54 | N,N—Di-(β-sulfato-ethyl)-sulfamoyl | 1,3-Propylene | Chlorine | Chlorine | 2,3,5,6-Tetra-chloro-... | Reddish-tinged blue (13) |
| 55 | N,N—Di-(β-sulfato-ethyl)-sulfamoyl | " | Bromine | Bromine | 2,3,5,6-Tetra-bromo-... | Reddish-tinged blue (13) |
| 56 | N,N—Di-(β-sulfato-ethyl)-sulfamoyl | " | Methyl | Methyl | 2,5-Dimethyl 3,6-dichloro-... | Reddish-tinged blue (13) |
| 57 | N,N—Di-(β-sulfato-ethyl)-sulfamoyl | " | Methyl | Chlorine | 2-Methyl-3,5,6-trichloro-... | Reddish-tinged blue (13) |
| 58 | N,N—Di-(β-sulfato-ethyl)-sulfamoyl | —CH(CH₃)—CH₂— | Chlorine | Chlorine | 2,3,5,6-Tetra-chloro-... | Reddish-tinged blue (13) |
| 59 | N,N—Di-(β-sulfato-ethyl)-sulfamoyl | " | Bromine | Bromine | 2,3,5,6-Tetra-bromo-... | Reddish-tinged blue (13) |
| 60 | N,N—Di-(β-sulfato-ethyl)-sulfamoyl | 1,3-Cyclohexylene | Chlorine | Chlorine | 2,3,5,6-Tetra-chloro-... | Reddish-tinged blue (13) |
| 61 | N,N—Di-(β-sulfato-ethyl)-sulfamoyl | Bis-(1,4-cyclo-hexylene)-methane | Chlorine | Chlorine | 2,3,5,6-Tetra-chloro-... | Reddish-tinged blue (13) |
| 62 | N,N—Di-(β-sulfato-ethyl)-sulfamoyl |  | Chlorine | Chlorine | 2,3,5,6-Tetra-chloro-... | Reddish-tinged blue (13) |
| 63 | N,N—Di-(β-sulfato-ethyl)-sulfamoyl | 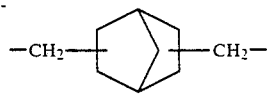 | Chlorine | Chlorine | 2,3,5,6-Tetra-chloro-... | Reddish-tinged blue (13) |
| 64 | N,N—Di-(β-sulfato-ethyl)-sulfamoyl | 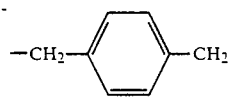 | Chlorine | Chlorine | 2,3,5,6-Tetra-chloro-... | Reddish-tinged blue (13) |

-continued

| | | Compound corresponding to formula (1A) | | | | |
|---|---|---|---|---|---|---|
| Ex. | Radical E | Radical W² | X¹ is ... | X² is ... | Compound (5) = ... 1,4-benzo-quinone | Color shade |
| 65 | N,N—Di-(β-sulfato-ethyl)-sulfamoyl | 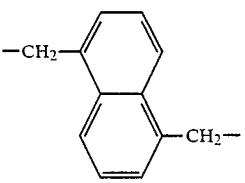 —CH₂— ... —CH₂— | Chlorine | Chlorine | 2,3,5,6-Tetra-chloro-... | Reddish-tinged blue (13) |
| 66 | N,N—Di-(β-sulfato-ethyl)-sulfamoyl | 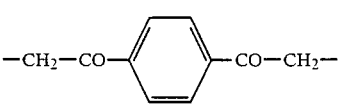 —CH₂—CO— ... —CO—CH₂— | Chlorine | Chlorine | 2,3,5,6-Tetra-chloro-... | Reddish-tinged blue (13) |
| 67 | N—(β-Sul-fatoethyl)-sulfamoyl | 1,2-Ethylene | Chlorine | Chlorine | 2,3,5,6-Tetra-chloro-... | Reddish-tinged blue (13) |
| 68 | N—(β-Sul-fatoethyl)-sulfamoyl | 1,3-Propylene | Chlorine | Chlorine | 2,3,5,6-Tetra-chloro-... | Reddish-tinged blue (13) |
| 69 | N—(β-Sul-fatoethyl)-sulfamoyl | —(CH₂)₂—N—(CH₂)₂—<br>        \|<br>       CO—CH₃ | Chlorine | Chlorine | 2,3,5,6-Tetra-chloro-... | Reddish-tinged blue (13) |
| 70 | N—(β-Sul-fatoethyl)-sulfamoyl | 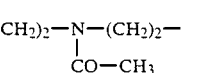 —(CH₂)₂—N     N—(CH₂)₂— | Chlorine | Chlorine | 2,3,5,6-Tetra-chloro-... | Reddish-tinged blue (13) |
| 71 | N—(β-Sul-foethyl)-sulfamoyl | 1,2-Ethylene | Chlorine | Chlorine | 2,3,5,6-Tetra-chloro-... | Reddish-tinged blue (13) |
| 72 | N—Methyl-N—(β-sul-foethyl)-sulfamoyl | 1,3-Propylene | Chlorine | Chlorine | 2,3,5,6-Tetra-chloro-... | Reddish-tinged blue (13) |
| 73 | N—Methyl-N—(β-sul-foethyl)-sulfamoyl | 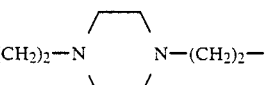 —CH₂—CH₂— ... — | Chlorine | Chlorine | 2,3,5,6-Tetra-chloro-... | Reddish-tinged blue (13) |
| 74 | N—Methyl-N—(β-sul-foethyl)-sulfamoyl | 1,5-Disulfo-naphth-3,7-ylene | Chlorine | Chlorine | 2,3,5,6-Tetra-chloro-... | Reddish-tinged blue (13) |
| 75 | N—Methyl-N—(β-sul-foethyl)-sulfamoyl | 1,2-Ethylene | Chlorine | Chlorine | 2,3,5,6-Tetra-chloro-... | Reddish-tinged blue (13) |
| 76 | N—[(Sulfo-phenyl)-sulfonyl]-sulfamoyl | " | Chlorine | Chlorine | 2,3,5,6-Tetra-chloro-... | Reddish-tinged blue (13) |
| 77 | N—[(β-Sul-fatoethyl)-sulfonyl-methyl]-sulfamoyl | 2-(4'Sulfo-phenyl)-1,3 propylene | Chlorine | Chlorine | 2,3,5,6-Tetra-chloro-... | Reddish-tinged blue (13) |
| 78 | N—β-(4-Sul-fophenyl)-ethyl-sulf-amoyl | 2-Sulfato-1,3-propylene | Chlorine | Chlorine | 2,3,5,6-Tetra-chloro-... | Reddish-tinged blue (13) |
| 79 | N—[4-Meth-oxy-3-(β-sulfato-ethylsulfonyl-phenyl]-sulfamoyl | 2-Sulfato-1,3-propylene | Chlorine | Chlorine | 2,3,5,6-Tetra-chloro-... | Reddish-tinged blue (13) |
| 80 | N—β-[2-Sul-fo-4-(β-sul-fatoethyl- | 1,2-Ethylene | Chlorine | Chlorine | 2,3,5,6-Tetra-chloro-... | Reddish-tinged blue (13) |

-continued

| | | Compound corresponding to formula (1A) | | | Compound (5) = ... 1,4-benzo- | |
|---|---|---|---|---|---|---|
| Ex. | Radical E | Radical W² | X¹ is ... | X² is ... | quinone | Color shade |
| | sulfonyl)-phenyl]-ethyl-sulfamoyl | | | | | |
| 81 | Carboxy | " | Methyl | Methyl | 2,5-Dimethyl-3,6-dichloro-... | Reddish-tinged blue (13) |

EXAMPLE 82

(a) 441 parts of the compound of the formula

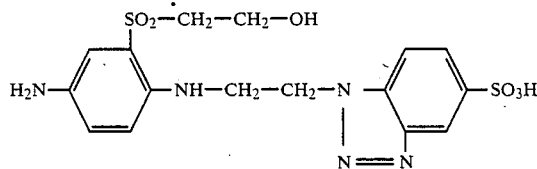

are dissolved in 2,000 parts of water at pH 6 and 65° C. 124 parts of chloranil are introduced, the pH being kept at a value of 6 to 6.5 by means of about 90 parts of sodium bicarbonate and the reaction temperature being kept at about 65° C. The mixture is stirred for a further ten hours, and the reaction product is then clarified at about 30° C., precipitated with a little sodium chloride, filtered off with suction, washed with 1,000 parts of 10% strength aqueous sodium chloride solution and dried at 70° C. under reduced pressure.

(b) 105 parts of the product obtained under (a) are introduced into 750 parts of 13% strength oleum at a temperature between 20° and 25° C. The reaction mixture is then stirred for about a further ten hours at this temperature; 48 parts of sodium peroxodisulfate are then added at such a rate that the reaction temperature can be kept at 20° to 25° C. The mixture is stirred for a further ten hours at this temperature and is then run onto ice, and the compound, according to the invention, which has been precipitated is filtered off and redissolved in about 1,000 parts of water the pH of which is adjusted to a value of 5 with sodium carbonate, and the compound is salted out with sodium chloride, if necessary after clarifying the solution beforehand in a customary manner.

The triphendioxazine compound according to the invention can also be obtained in the form of its sodium salt by evaporating or spray drying the clarified synthesis solution. Expressed in the form of the free acid, it has the probable formula

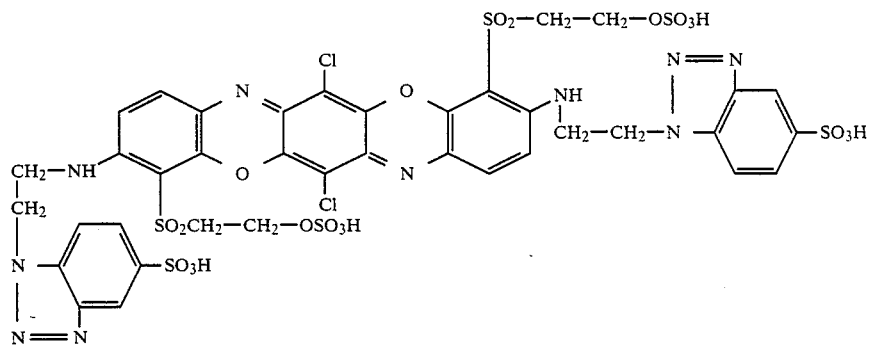

(each of the sulfatoethylsulfonyl groups can also be attached in the other ortho-position relative to the sulfobenzotriazolylethylamino group, but is more probably in the position indicated in the above formula). This compound according to the invention possesses good fiber-reactive properties as a dyestuff. It dyes the materials mentioned in the description, in particular cellulose fiber materials, such as cotton, by the procedures customary and known in the art for the application and fixation of fiber-reactive dyestuffs, in deep, clear, reddish-tinged blue shades (corresponding to the color coefficient 13 of the Color Index Hue Indication Chart) having good fastness properties, such as, in particular, good fastness to light in the dry or moist, such as moistened with drinking water, dyeing, good fastness to light in alkaline perspiration, fastness to chlorinated water, fastness to hypochlorite, fastness to alkaline perspiration, fastness to washing, even in the presence of perborates, fastness to wet storage and resistance to acid fading. In aqueous solution it exhibits an absorption maximum at 604 nm in the visible range.

(c) The 4-[β-(5'-sulfobenzotriazol-1'-yl)-ethylamino]-3-(β-hydroxyethylsulfonyl)-aniline employed under (a) can, for example, be prepared as follows:

266 parts of 4-nitro-2-(β-hydroxyethylsulfonyl)-chlorobenzene are added to a mixture, preheated to 30° C., of 243 parts of 5-sulfo-1-(β-aminoethyl)-benzotriazole in 1,000 parts of water and 600 parts of triethanolamine. The mixture is heated to 100° to 110° C. in the course of two hours, part of the water distilling off. The mixture is stirred for a further ten hours at 115° to 120° C. in order to achieve quantitative reaction, and 3,000 parts of water are then added at 100° C. and the solution is clarified at 80° to 90° C. On cooling, the sodium salt of 4-[β-(5'-sulfobenzotriazol-1'-yl)-ethylamino]-3-(β-hydroxyethylsulfonyl)nitrobenzene crystallizes out from the aqueous medium in a high yield and purity.

(d) The nitro compound from (c) is reduced to the aniline compond by catalytic hydrogenation by dissolving 236 parts of the nitro compound in 1,000 parts of water (instead of this, it can also be employed in the form of the solution above) and hydrogenating it in the presence of a Pd-on-charcoal catalyst in an autoclave at a temperature of up to 100° C. and a hydrogen pressure of 50 bar. The catalyst is then filtered off and the filtrate is cooled and acidified. The aniline compound crystallizes out therefrom in good yield and high purity.

The hydrogenation solution can also be used without further treatment for reaction (a).

(e) The 1-(β-aminoethyl)-5-sulfobenzo-1,2,3-triazole employed under (c) can be prepared by procedures known from the literature, for example also analagously to the Working Examples 1 and 2 above, by reacting 4-sulfo-2-nitrochlorobenzene with ethylenediamine, reducing the resulting 4-sulfo-2-nitro-1-N-(β-aminoethyl)-aniline and then diazotizing the latter, in the course of which the desired cyclization to give the benzotriazole takes place.

EXAMPLES 83 TO 92

Further triphendioxazine compounds, according to the invention, corresponding to the general formula (1B)

general formula (5) and which can be seen in the appropriate Tabular Example, with a compound of the general formula (4B)

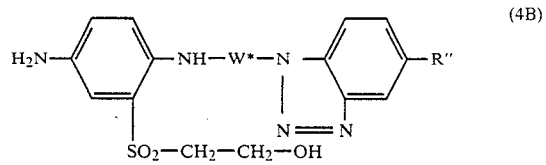
(4B)

(R" in formula (4B) being the hydroxy derivative of R" in formula (1B), if R" in that formula contains a sulfato group), and subsequent sulfation and cyclization. These triphendioxazine compounds according to the invention also possess very good fiber-reactive properties as dyestuffs and afford, on the materials mentioned in the description, such as, in particular, cellulose fiber materials, deep, fast dyeings having the color shade on cotton indicated in the appropriate tabular example (with the color coefficient indicated in parentheses of the Color Index Hue Indication Chart).

The following absorption maxima ($\lambda_{max}$) in the visible range were determined in aqueous solution for the triphendioxazine compounds described in Tabular Examples 83 to 85:

Example 83: 604 nm
Example 84: 612 nm
Example 85: 612 nm
Example 86: 606 nm.

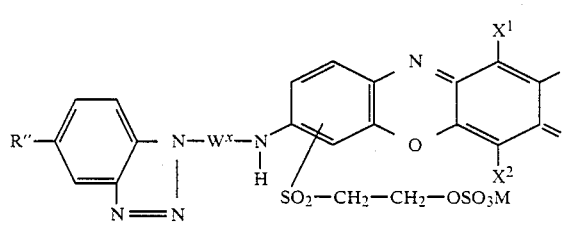
(1B)

(in which M has the meaning indicated in the description) are described by means of their radicals in the Tabular Examples below (in these, the radical W* represents in each case the group of "mirror image" structure of the radical $W^x$ shown). They can be prepared in a manner according to the invention, for example analogously to the above Working Examples, by reacting a 1,4-benzoquinone compound which corresponds to the

| | | | | | Compound (5) = ...1,4-benzo- | |
|---|---|---|---|---|---|---|
| Ex. | Group R" | Radical W* | $X^1$ is ... | $X^2$ is ... | quinone | Color shade |
| 83 | Sulfo | 1.2-Ethylene | Bromine | Bromine | 2,3,5,6-Tetrabromo-... | Reddish-tinged blue (13) |
| 84 | Sulfo | 1.3-Propylene | Chlorine | Chlorine | 2,3,5,6-Tetrachloro-... | Reddish-tinged blue (13) |
| 85 | Sulfo | " | Bromine | Bromine | 2,3,5,6-Tetrabromo-... | Reddish-tinged blue (13) |
| 86 | Sulfo | —CH(CH₃)—CH₂— | Chlorine | Chlorine | 2,3,5,6-Tetrachloro-... | Reddish-tinged blue (13) |
| 87 | Sulfo | 2-Sulfato-1,3-propylene | Chlorine | Chlorine | 2,3,5,6-Tetrachloro-... | Reddish-tinged blue (13) |
| 88 | Sulfo | 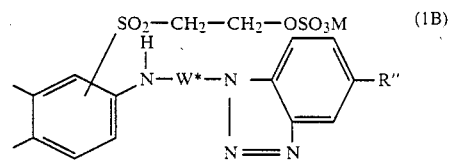 | Chlorine | Chlorine | 2,3,5,6-Tetrachloro-... | Reddish-tinged blue (13) |
| 89 | Sulfo | 1,4-(Bis-methylene)-phenylene | Chlorine | Chlorine | 2,3,5,6-Tetrachloro-... | Reddish-tinged blue (13) |
| 90 | Hydrogen | 1,5-Disulfo-naphth-3,7-ylene | Chlorine | Chlorine | 2,3,5,6-Tetrachloro-... | Greenish-tinged blue (15) |
| 91 | β-Sulfato-ethyl- | 2-Sulfato-1,3-propylene | Chlorine | Chlorine | 2,3,5,6-Tetrachloro-... | Reddish-tinged blue (13) |

| | Compound corresponding to formula (1B) | | | | | |
|---|---|---|---|---|---|---|
| Ex. | Group R'' | Radical W* | $X^1$ is... | $X^2$ is... | Compound (5) = ...1,4-benzo-quinone | Color shade |
| 92 | β-Sulfatoethylsulfonyl | Sulfophen-1,4-ylene | Chlorine | Chlorine | 2,3,5,6-Tetrachloro-... | Greenish-tinged blue (15) |

We claim:

1. A compound of the formula

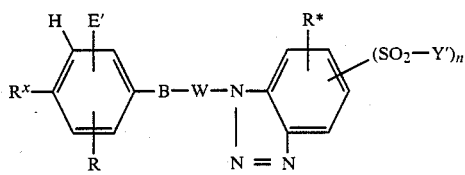

in which:

$R^x$ denotes $H_2N-$ or $O_2N-$;

Y' denotes the vinyl group, the β-hydroxyethyl group or an ethyl group containing, in the β-position, a substituent which can be eliminated by means of an alkali;

B is an oxygen or sulfur atom or an amino group of the formula $-NH-$ or $-N(R')-$ in which R' is alkyl of 1 to 6 carbon atoms unsubstituted or substituted by 1 or 2 substituents selected from the group consisting of chlorine, alkoxy of 1 to 4 carbon atoms benzoylamino, sulfobenzoylamino, alkanoylamino of 2 to 5 carbon atoms, hydroxy, sulfato, phosphato, phosphono, acetyloxy, sulfo, carboxy and phenyl unsubstituted or substituted by substituents selected from alkyl of 1 to 4 carbon atoms, alkoxy of 1 to 4 carbon atoms and sulfo;

E' denotes hydrogen, a sulfo or carboxy group or a group of the formula $-SO_2-Y'$, or E' is a sulfonamide group of the formula $-SO_2-NR^1R^2$, in which $R^1$ is a hydrogen or an alkylene of 2 to 6 carbon atoms substituted by sulfo or sulfato, or is an alkylene of 2 to 6 carbon atoms substituted by sulfo or sulfato and interrupted by 1 or 2 hetero groups selected from the groups of the formulae $-O-$, $-S-$, $-NH-$ and $-N(R')-$ in which R' has one of the meanings given above, or $R^1$ is an alkylene of 2 to 6 carbon atoms substituted by carboxy or phosphato, or is an alkylene of 1 to 3 carbon atoms substituted by phosphono, or is naphthyl or phenyl or naphthyl or phenyl substituted by substituents which are selected from the group consisting of methyl, methoxy, ethoxy, chlorine, carboxy and sulfo, and $R^2$ is hydrogen or is alkyl of 1 to 6 carbon atoms unsubstituted or substituted by 1 or 2 substituents selected from the group consisting of hydroxy, sulfato, carboxy, sulfo and methoxy, or E' is a sulfonamide group of the formula $-SO_2-NH-SO_2-R^3$ in which $R^3$ is alkyl of 1 to 6 carbon atoms unsubstituted or substituted by 1 or 2 substituents selected from the group consisting of chlorine, alkoxy of 1 to 4 carbon atoms, benzoylamino, sulfobenzoylamino, alkanoylamino of 2 to 5 carbon atoms, hydroxy, sulfato, phosphato, phosphono, acetyloxy, sulfo, carboxy and phenyl, or $R^3$ is phenyl unsubstituted or substituted by 1 or 2 sulfo groups;

W is alkylene of 1 to 6 carbon atoms which may be interrupted by 1 or 2 hetero groups which are selected from groups of the formulae $-O-$, $-S-$, $-SO_2-$, $-CO-$, $-1,4$-piperidino, $-NH-$ and $-N(R^o)-$ in which $R^o$ has one of the meanings of R' or is alkanoyl of 2 to 5 carbon atoms, and the alkylene W is unsubstituted or substituted by 1 or 2 substituents selected from the group consisting of chlorine, alkoxy of 1 to 4 carbon atoms, benzoylamino, sulfobenzoylamino, alkanoylamino of 2 to 5 carbon atoms, hydroxy, sulfato, phosphato, phosphono, acetyloxy, sulfo, carboxy and phenyl unsubstituted or substituted by substituents selected from alkyl of 1 to 4 carbon atoms, alkoxy of 1 to 4 carbon atoms and sulfo, or W is an alkylene-phenylene, phenylene-alkylene, phenylene-alkylene-phenylene or alkylene-phenylene-alkylene group, the alkylene moieties of which are of 1 to 6 carbon atoms unsubstituted or substituted by 1 or 2 substituents selected from chlorine, alkoxy of 1 to 4 carbon atoms, benzoylamino, sulfobenzoylamino, alkanoylamino of 2 to 5 carbon atoms, hydroxy, sulfato, phosphato, phosphono, acetyloxy, sulfo, carboxy and phenyl unsubstituted or substituted by substituents selected from alkyl of 1 to 4 carbon atoms, alkoxy of 1 to 4 carbon atoms and sulfo, and interrupted or non-interrupted by 1 or 2 hetero groups selected from those mentioned above, and the phenylene moieties of which are unsubstituted or substituted by 1 or 2 substituents selected from the group of substituents consisting of sulfo, carboxy, sulfamoyl, carbamoyl, methyl, ethyl, methoxy, ethoxy, nitro, chlorine, amino and amino substituted by alkyl of 1 to 4 carbon atoms, phenyl and/or benzyl, or W is phenylene or naphthylene, or phenylene or naphthylene both of which are substituted by substituents selected from alkyl or 1 to 4 carbon atoms, alkoxy of 1 to 4 carbon atoms, halogen, sulfo, carboxy, sulfamoyl, carbamoyl, carbamoyl which is mono- or disubstituted by phenyl, alkyl of 1 to 4 carbon atoms, phenylalkyl with an alkyl of 1 to 4 carbon atoms and/or cycloalkyl of 5 to 8 carbon atoms, sulfamoyl which is mono- or disubstituted by alkyl of 1 to 4 carbon atoms, phenyl, phenylalkyl with an alkyl of 1 to 4 carbon atoms and/or cycloalkyl of 5 to 8 carbon atoms, trifluoromethyl, benzoylamino, sulfobenzoylamino, alkanoylamino of 2 to 5 carbon atoms, nitro, amino and amino mono- or disubstituted by alkyl of 1 to 4 carbon atoms, phenyl, phenylalkyl with an alkyl of 1 to 4 carbon atoms and/or cycloalkyl of 5 to 8 carbon atoms, or W is one of the above-mentioned alkylene and arylene moieties which are connected with one another by one of the above-mentioned hetero groups, or W is a cycloalkylene of 5 to 10 carbon atoms unsubstituted or substituted by alkyl of 1 to 4 carbon atoms, or is an alkylene-cycloalkylene or cycloalkylene-alkylene or alkylene-cycloalkylene-alkylene the alkylene moieties of which are of 1 to 4 carbon atoms and the cycloalkylene moieties of which are of 5 to 8 carbon atoms and may be substituted by alkyl of 1 to 4 carbon atoms;

R is hydrogen, alkyl of 1 to 6 carbon atoms, alkoxy of 1 to 5 carbon atoms, halogen, carboxy or sulfo;

n denotes the number 0 or 1, but n is only zero if E' is a group $-SO_2Y'$; in which Y' is β-sulfatoethyl; and R* denotes a hydrogen atom, an alkyl group having 1 to 4 carbon atoms, an alkoxy group having 1 to 4 carbon atoms, a halogen atom or a carboxy or sulfo group.

2. A compound as claimed in claim 1, wherein $R^x$ is $H_2N-$.

3. A compound as claimed in claim 1, wherein $R^x$ is $O_2N-$.

4. A compound as claimed in claim 1, wherein the E' group is attached in the ortho-position relative to the radical B.

5. A compound as claimed in claim 1, wherein B denotes $-NH-$.

6. A compound as claimed in claim 2, wherein B denotes $-NH-$.

7. A compound as claimed in claim 3 wherein B denotes $-NH-$.

8. A compound as claimed in claim 1, wherein R denotes hydrogen.

9. A compound as claimed in claim 1, wherein E' denotes sulfo.

10. A compound as claimed in claim 1, wherein W denotes 1,3-phenylene, 1,4-phenylene, β-(p-phenylene)-ethylene, 2-(4'-sulfophenyl)-1,3-propylene, 2-sulfato-1,3-propylene, or a group of the formula $-CH_2-CH_2-O-CH_2-CH_2-$, $-CH_2-CH_2-NH-CH_2-CH_2-$ or $-CH_2-CH_2-N(CH_3)-CH_2-CH_2-$.

11. A compound as claimed in claim 1, wherein W denotes a group of formula

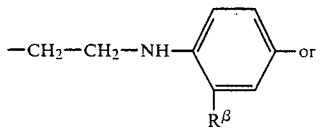

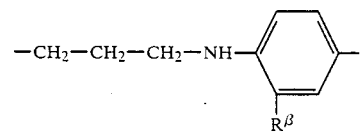

in which $R^β$ is hydrogen or sulfo.

12. A compound as claimed in claim 1, wherein W denotes 1,2-ethylene, 1,3-propylene, 1,4-butylene or isopropylene.

13. A compound as claimed in claim 1, wherein E' denotes β-sulfatoethylsulfonyl, N,N-di(β-sulfatoethyl)-sulfamoyl, N-(β-sulfatoethyl)-sulfamoyl, N-(β-sulfoethyl)-sulfamoyl or N-methyl-N-(β-sulfoethyl)-sulfamoyl.

14. A compound as claimed in claim 1, wherein Y' denotes β-sulfatoethyl.

15. A compound as claimed in claim 2, wherein W denotes 1,2-ethylene, 1,3-propylene, 1,4-butylene or isopropylene.

16. A compound as claimed in claim 2, wherein E' denotes β-sulfatoethylsulfonyl, N,N-di-(β-sulfatoethyl)-sulfamoyl, N-(β-sulfatoethyl)-sulfamoyl, N-(β-sulfoethyl)-sulfamoyl or N-methyl-N-(β-sulfoethyl)-sulfamoyl.

17. A compound as claimed in claim 2, wherein Y' denotes β-sulfatoethyl.

18. A compound as claimed in claim 3, wherein W denotes 1,2-ethylene, 1,3-propylene, 1,4-butylene or isopropylene.

19. A compound as claimed in claim 3, wherein Y' denotes β-sulfatoethyl.

* * * * *